(12) United States Patent
Ray et al.

(10) Patent No.: US 12,083,144 B2
(45) Date of Patent: *Sep. 10, 2024

(54) DOSAGE FORM FOR TREATING SEVERE ASTHMA

(71) Applicant: University of Pittsburgh—Of the Commonwealth System of Higher Education, Pittsburgh, PA (US)

(72) Inventors: Anuradha Ray, Pittsburgh, PA (US); Prabir Ray, Pittsburgh, PA (US); Sally Ellen Wenzel, Pittsburgh, PA (US); Timothy B. Oriss, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 463 days.

This patent is subject to a terminal disclaimer.

(21) Appl. No.: 17/466,454

(22) Filed: Sep. 3, 2021

(65) Prior Publication Data

US 2022/0062322 A1    Mar. 3, 2022

Related U.S. Application Data

(60) Continuation of application No. 16/539,383, filed on Aug. 13, 2019, now Pat. No. 11,129,846, which is a division of application No. 15/903,505, filed on Feb. 23, 2018, now Pat. No. 10,420,792.

(60) Provisional application No. 62/463,243, filed on Feb. 24, 2017.

(51) Int. Cl.
*A61K 31/713* (2006.01)
*A61K 31/573* (2006.01)
*A61P 11/06* (2006.01)

(52) U.S. Cl.
CPC ............ *A61K 31/713* (2013.01); *A61P 11/06* (2018.01); *A61K 31/573* (2013.01); *A61K 2300/00* (2013.01)

(58) Field of Classification Search
CPC ................ A61K 31/713; A61K 31/573; A61K 2300/00; A61P 11/06
USPC ...... 424/9.1; 435/6.1, 91.1, 91.31, 455, 458; 514/1, 44 A; 536/23.1, 24, 5
See application file for complete search history.

(56) References Cited

U.S. PATENT DOCUMENTS

| | | | |
|---|---|---|---|
| 10,420,792 B2* | 9/2019 | Ray | A61P 11/06 |
| 11,129,846 B2* | 9/2021 | Ray | A61P 11/06 |
| 2014/0030218 A1 | 1/2014 | Udalova et al. | |
| 2016/0009772 A1 | 1/2016 | Demartino et al. | |
| 2016/0347844 A1 | 12/2016 | Dekruyff et al. | |
| 2017/0081667 A1 | 3/2017 | Chen et al. | |

FOREIGN PATENT DOCUMENTS

WO    2013121034 A1    8/2013

OTHER PUBLICATIONS

Balzar et al., "Mast Cell Phenotype, Location, and Activation in Severe Asthma", Am J Respir Crit Care Med, 2011, pp. 299-309, vol. 183.
Braciale et al., "Regulating the adaptive immune response to respiratory virus infection", Nature Reviews Immunology, 2012, pp. 295-305, vol. 12.
Cella et al., "Ligation of CD40 on Dendritic Cells Triggers Production of High Levels of Interleukin-12 and Enhances T Cell Stimulatory Capacity: T-T Help via APC Activation", J. Exp. Med., 1996, pp. 747-752, vol. 184.
Chambers et al., "Distinct endotypes of steroid-resistant asthma characterized by IL-17Ahigh and IFN-Yhigh immunophenotypes: Potential benefits of calcitriol", J Allergy Clin Immunol, 2015, pp. 628-637, vol. 136.
Chesne et al., "Prime role of IL-17A in neutrophilia and airway smooth muscle contraction in a house dust mite-induced allergic asthma model", J Allergy Clin Immunol, 2015, pp. 1-8, vol. 135:6.
Chung et al., "International ERS/ATS Guidelines on Definition, Evaluation and Treatment of Severe Asthma", Eur Respir J., 2014, pp. 343-373, vol. 43:2.
Corey, "Chemical modification: the key to clinical application of RNA interference?", The Journal of Clinical Investigation, 2007, pp. 3615-3622, vol. 117:12.
Courties et al., "In Vivo Silencing of the Transcription Factor IRF5 Reprograms the Macrophage Phenotype and Improves Infarct Healing", J Am Coll Cardiol, 2014, pp. 1556-1566, vol. 63.
D'Andrea et al., "Production of Natural Killer Cell Stimulatory Factor (Interleukin 12) by Peripheral Blood Mononuclear Cells", J. Exp. Med., 1992, pp. 1387-1398, vol. 176.
Eames et al., "Interferon regulatory factor 5 in human autoimmunity and murine models of autoimmune disease", Translational Research, 2016, pp. 167-182, vol. 167.
Eng et al., "The Role and Immunobiology of Eosinophils in the Respiratory System: a Comprehensive Review", Clinic Rev Allerg Immunol, 2016, pp. 140-158, vol. 50.
Fei et al., "TNF-a from inflammatory dendritic cells (DCs) regulates lung IL-17A/IL-5 levels and neutrophilia versus eosinophilia during persistent fungal infection", PNAS, 2011, pp. 5360-5365, vol. 108:13.
Gately et al., "The Interleukin-12/Interleukin-12-Receptor System: Role in Normal and Pathologic Immune Responses", Annu. Rev. Immunol., 1998, pp. 495-521, vol. 16.
Gauthier et al., "Evolving Concepts of Asthma", Am J Respir Crit Care Med, 2015, pp. 660-668, vol. 192:6.
Jackson et al., "IL-33-Dependent Type 2 Inflammation during Rhinovirus-induced Asthma Exacerbations in Vivo", Am J Respir Crit Care Med, 2014, pp. 1373-1382, vol. 190:12.

(Continued)

*Primary Examiner* — Jane J Zara
(74) *Attorney, Agent, or Firm* — The Webb Law Firm

(57) ABSTRACT

Methods are provided for treating corticosteroid-resistant asthma in a patient, comprising decreasing Interferon Regulatory Factor 5 (IRF5) activity in the patient. Antisense or RNA interference reagents and methods can be used to decrease IRF5 activity in the patient.

19 Claims, 11 Drawing Sheets

Specification includes a Sequence Listing.

(56) References Cited

OTHER PUBLICATIONS

Jang et al., "Distinct chemokine and cytokine gene expression pattern of murine dendritic cells and macrophages in response to Mycobacterium tuberculosis infection", J. Leukoc. Biol., 2008, pp. 1264-1270, vol. 84.

Jarjour et al., "Severe Asthma: Lessons Learned from the National Heart, Lung, and Blood Institute Severe Asthma Research Program", Am J Respir Crit Care Med, 2012, pp. 356-362, vol. 185:4.

Khare et al., "Cutting Edge: Inhaled Antigen Upregulates Retinaldehyde Dehydrogenase in Lung CD103+ but Not Plasmacytoid Dendritic Cells to Induce Foxp3 De Novo in CD4+ T Cells and Promote Airway Tolerance", The Journal of Immunology, 2013, pp. 25-29, vol. 191.

Kim et al., "Respiratory Dendritic Cell Subsets Differ in Their Capacity to Support the Induction of Virus-Specific Cytotoxic CD8+ T Cell Responses", PLOS One, 2009, pp. 1-13, vol. 4:1.

Kirby et al., "Alveolar Macrophages Transport Pathogens to Lung Draining Lymph Nodes", The Journal of Immunology, 2009, pp. 1983-1989, vol. 183.

Krausgruber et al., "IRF5 promotes inflammatory macrophage polarization and TH1-TH17 responses", Nature Immunology, 2011, pp. 231-238, vol. 12:3.

Krishnamoorthy et al., "Activation of c-Kit in dendritic cells regulates T helper cell differentiation and allergic asthma", Nature Medicine, 2008, pp. 565-573, vol. 14:5.

Leavy, "An IFNγ bias in severe asthma", Nat Rev Immunol, 2015, pp. 466-467, vol. 15:8.

Luyster et al., "Sleep Quality and Asthma Control and Quality of Life in Non-Severe and Severe Asthma", Sleep Breath, 2012, pp. 1129-1137, vol. 16:4.

Macatonia et al., "Dendritic Cells Produce IL-12 and Direct the Development of Th1 Cells from Naive CD4+ T Cells". The Journal of Immunology, 1995, pp. 5071-5079, vol. 154.

Mancl et al., "Two Discrete Promoters Regulate the Alternatively Spliced Human Interferon Regulatory Factor-5 Isoforms", The Journal of Biological Chemistry, 2005, pp. 21078-21090, vol. 280:22.

O'Connell et al., "IFN-γ-induced JAK/STAT, but not NF-kB, signaling pathway is insensitive to glucocorticoid in airway epithelial cells", Am J Physiol Lung Cell Mol Physiol, 2015, pp. L348-L359, vol. 309.

O'Garra et al., "The role of macrophage- and dendritic cell-derived IL12 in Th1 phenotype development", Res Immunol, 1995, pp. 466-472, vol. 146:7-8.

Oriss et al., "Dynamics of Dendritic Cell Phenotype and Interactions with CD4+ T Cells in Airway Inflammation and Tolerance", The Journal of Immunology, 2005, pp. 854-863, vol. 174.

Oriss et al., "Irf5 as an Upstream Regulator of Severe Steroid-Refractory Asthma", Am J Respir Crit Care Med, 2017, Abstract only.

Oriss et al., "IRF5 distinguishes severe asthma in humans and drives Th1 phenotype and airway hyperreactivity in mice", JCI Insight, 2017, pp. 1-16, vol. 2:10.

Plantinga et al., "Conventional and Monocyte-Derived CD11b+ Dendritic Cells Initiate and Maintain T Helper 2 Cell-Mediated Immunity to House Dust Mite Allergen", Immunity, 2013, pp. 322-335, vol. 38.

Purtha et al., "Spontaneous mutation of the Dock2 gene in Irf5-/- mice complicates interpretation of type I interferon production and antibody responses", 2012, pp. E898-E904.

Raundhal et al., "High IFN-γ and low SLPI mark severe asthma in mice and humans", J Clin Invest., 2015, pp. 3037-3050, vol. 125:8.

Ray et al., "Emerging molecular phenotypes of asthma", Am J Physiol Lung Cell Mol Physiol, 2015, pp. L130-L140, vol. 308.

Ray et al., "Current concepts of severa asthma", J Clin Invest., 2016, pp. 2394-2403, vol. 126:7.

Shannon et al., "Differences in Airway Cytokine Profile in Severe Asthma Compared to Moderate Asthma", Chest, 2008, pp. 420-426, vol. 133.

Sullivan et al., "Extent, patterns, and burden of uncontrolled disease in severe or difficult-to-treat asthma", Allergy, 2007, pp. 126-133, vol. 62.

Truyen et al., "Evaluation of airway inflammation by quantitative Th1/Th2 cytokine mRNA measurement in sputum of asthma patients", Thorax, 2006, pp. 202-208, vol. 61.

Vermaelen et al., "Specific Migratory Dendritic Cells Rapidly Transport Antigen from the Airways to the Thoracic Lymph Nodes", J. Exp. Med., 2001, pp. 51-60, vol. 193:1.

Voraphani et al., "An Airway Epithelial iNOS-DUOX2-Thyroid Peroxidase Metabolome Drives Th1/Th2 Nitrative Stress in Human Severe Asthma", Mucosal Immunol, 2014, pp. 1175-1185, vol. 7:5.

Watts et al., "Gene silencing by siRNAs and antisense oligonucleotides in the laboratory and the clinic", J Pathol, 2012, pp. 365-379, vol. 226:2.

Wenzel, "Asthma phenotypes: the evolution from the clinical to molecular approaches", Nature Medicine, 2012, pp. 716-725, vol. 18:5.

Williams et al., "Transcription factor IRF4 drives dendritic cells to promote Th2 differentiation", Nature Communications, 2013, pp. 1-12.

Zylberberg et al., "Pharmaceutical liposomal drug delivery: a review of new delivery systems and a look at the regulatory landscape", Drug Deliv, 2016, pp. 3319-3329, vol. 23:9.

\* cited by examiner

NP_116032.1 interferon regulatory factor 5 isoform b [Homo sapiens]

MNQSIPVAPTPPRRVRLKPWLVAQVNSCQYPGLQWVNGEKKLFCIPWRHATRHGPSQDGDNTIFKAWAKE
TGKYTEGVDEADPAKWKANLRCALNKSRDFRLIYDGPRDMPPQPYKIYEVCSNGPAPTDSQPPEDYSFGA
GEEEEEEEELQRMLPSLSLTEDVKWPPTLQPPTLRPPTLQPPTLQPPVVLGPPAPDPSPLAPPPGNPAGF
RELLSEVLEPGPLPASLPPAGEQLLPDLLISPHMLPLTDLEIKFQYRGRPPRALTISNPHGCRLFYSQLE
ATQEQVELFGPISLEQVRFPSPEDIPSDKQRFYTNQLLDVLDRGLILQLQGQDLYAIRLCQCKVFWSGPC
ASAHDSCPNPIQREVKTKLFSLEHFLNELILFQKGQTNTPPPFEIFFCFGEEWPDRKPREKKLITVQVVP
VAARLLLEMFSGELSWSADSIRLQISNPDLKDRMVEQFKELHHIWQSQQRLQPVAQAPPGAGLGVGQGPW
PMHPAGMQ

*Fig. 1A*

AAA96056.1 interferon regulatory factor 5 [Homo sapiens]

MNQSIPVAPTPPRRVRLKPWLVAQVNSCQYPGLQWVNGEKKLFCIPWRHATRHGPSQDGDNTIFKAWAKE
TGKYTEGVDEADPAKWKANLRCALNKSRDFRLIYDGPRDMPPQPYKIYEVCSNGPAPTDSQPPEDYSFGA
GEEEEEEEELQRMLPSLSLTDAVQSGPHMTPYSLLKEDVKWPPTLQPPTLQPPVVLGPPAPDPSPLAPPP
GNPAGFRELLSEVLEPGPLPASLPPAGEQLLPDLLISPHMLPLTDLEIKFQYRGRPPRALTISNPHGCRL
FYSQLEATQEQVELFGPISLEQVRFPSPEDIPSDKQRFYTNQLLDVLDRGLILQLQGQDLYAIRLCQCKV
FWSGPCASAHDSCPNPIQREVKTKLFSLEHFLNELILFQKGQTNTPPPFEIFFCFGEEWPDRKPREKKLI
TVQVVPVAARLLLEMFSGELSWSADSIRLQISNPDLKDRMVEQFKELHHIWQSQQRLQPVAQAPPGAGLG
VGQGPWPMHPAGMQ

*Fig. 1B*

NM_032643.4 - Homo sapiens interferon regulatory factor 5 (IRF5), transcript variant 2, mRNA

```
GTCCAGCTGCGCCTGGAAAGCGAGCTCGGACCCCTCTGCCATGAACCAGTCCATCCCAGTGGCTCCCACC
CCACCCCGCCGCGTGCGGCTGAAGCCCTGGCTGGTGGCCCAGGTGAACAGCTGCCAGTACCCAGGGCTTC
AATGGGTCAACGGGGAAAAGAAATTATTCTGCATCCCCTGGAGGCATGCCACAAGGCATGGTCCCAGCCA
GGACGGAGATAACACCATCTTCAAGGCCTGGGCCAAGGAGACAGGGAAATACACCGAAGGCGTGGATGAA
GCCGATCCGGCCAAGTGGAAGGCCAACCTGCGCTGTGCCCTTAACAAGAGCCGGGACTTCCGCCTCATCT
ACGACGGGCCCCGGGACATGCCACCTCAGCCCTACAAGATCTACGAGGTCTGCTCCAATGGCCCTGCTCC
CACAGACTCCCAGCCCCTGAGGATTACTCTTTTGGTGCAGGAGAGGAGGAGGAAGAAGAGGAAGAGCTG
CAGAGGATGTTGCCAAGCCTGAGCCTCACAGAGGATGTCAAGTGGCCGCCCACTCTGCAGCCGCCCACTC
TGCGGCCGCCTACTCTGCAGCCGCCCACTCTGCAGCCGCCCGTGGTGCTGGGTCCCCTGCTCCAGACCC
CAGCCCCTGGCTCCTCCCCTGGCAACCCTGCTGGCTTCAGGGAGCTTCTCTCTGAGGTCCTGGAGCCT
GGGCCCTGCCTGCCAGCCTGCCCCTGCAGGCGAACAGCTCCTGCCAGACCTGCTGATCAGCCCCCACA
TGCTGCCTCTGACCGACCTGGAGATCAAGTTTCAGTACCGGGGGCGGCCACCCCGGGCCCTCACCATCAG
CAACCCCCATGGCTGCCGGCTCTTCTACAGCCAGCTGGAGGCCACCCAGGAGCAGGTGGAACTCTTCGGC
CCCATAAGCCTGGAGCAAGTGCGCTTCCCCAGCCCTGAGGACATCCCCAGTGACAAGCAGCGCTTCTACA
CGAACCAGCTGCTGGATGTCCTGGACCGCGGGCTCATCCTCCAGCTACAGGGCCAGGACCTTTATGCCAT
CCGCCTGTGTCAGTGCAAGGTGTTCTGGAGCGGGCCTTGTGCCTCAGCCCATGACTCATGCCCCAACCCC
ATCCAGCGGGAGGTCAAGACCAAGCTTTTCAGCCTGGAGCATTTTCTCAATGAGCTCATCCTGTTCCAAA
AGGGCCAGACCAACACCCCACCACCCTTCGAGATCTTCTTCTGCTTTGGGGAAGAATGGCCTGACCGCAA
ACCCCGAGAGAAGAAGCTCATTACTGTACAGGTGGTGCCTGTAGCAGCTCGACTGCTGCTGGAGATGTTC
TCAGGGGAGCTATCTTGGTCAGCTGATAGTATCCGGCTACAGATCTCAAACCCAGACCTCAAAGACCGCA
TGGTGGAGCAATTCAAGGAGCTCCATCACATCTGGCAGTCCCAGCAGCGGTTGCAGCCTGTGGCCCAGGC
CCCTCCTGGAGCAGGCCTTGGTGTTGGCCAGGGGCCCTGGCCTATGCACCCAGCTGGCATGCAATAACAA
GGCTGCAGACGGTGACTGGCCCTGGCTTCCTGGGTGGCGGTGCGGACTGATGTGGAGATGTGACAGCCCC
GATGAGCACCTGGCTGGCTGCAGGGTCCTACCTCTGGGTTTCCTGGAAGTGGATTTGGGCCAAGAAGGAG
AGGGAGAAAGGCCCGAGCCCCTGCCTTCCCGGGCCTTTCTCTCCTGGGCTGTCTCTGGTCTGGTCAGCCT
GGCTCTCGGGAAATTCAGCCATGAGCAGGGAAAGAACTCTCCCAACCCTGGGGCCTAGCTGTATAGGAGG
AATTGCCTAAGGGTGGCCCACTCTTGTGATTGCCCATTTCCTCTGGCAACAAAAGCCAGAGTGTTGTGG
GCCAAGTCCCCCACAGGGCCTCTGCAGGGCATGGCCCTGATTTCCTGGTTTGAGACTCACTTCCTCAT
CTCCCTGTCCTCTGAGATAATATGAGTGAGCACTTAGGTATCATATCAGATGCTCAAGGCTGGCAGCTAC
CCCCTTCTTGAGAGTCCAAGAACCTGGAGCAGAAATAATTTTTATGTATTTTTGGATTAATGAATGTTAA
AAACAGACTCAGCTGTTTCTTTCCTTTTACTACTACCAGTTGCTCCCATGCTGCTCCACCAGGCCCTGTT
TCGGATGCCAACTGGCCCACTCCCCAAGCACTTGCCCCAGCTTGCGACCATTGGCACTGGGAGGGCCTG
GCTTCTGGGCTGATGGGTCAGTTGGGCCTTCATAAACACTCACCTGGCTGGCTTTGCCTTCCAGGAGGAA
GCTGGCTGAAGCAAGGGTGTGGAATTTAAATGTGTGCACAGTCTGGAAAACTGTCAGAATCAGTTTCC
CATAAAAGGGTGGGCTAGCATTGCAGCTGCATTTGGGACCATTCAAATCTGTCACTCTCTTGTGTATATT
CCTGTGCTATTAAATATATCAGGGCAGTGCATGTAAATCATCCTGATATATTTAATATATTTATTATATT
GTCCCCCGAGGTGGGGACAGTGAGTGAGTTCTCTTAGTCCCCCAGAGCTGGTTGTTAAAGAGCCTGGCA
CCTACCCGCTCTCACTTCATCTGTGTCATCTCTGCACACTCCAGCCCACTTTCTGCCTTCAGCCATTGAG
TGGAAGCTGCCCCAGGCCCTTACCAGGTGCAGATGCCCAATCTTGATGCCCAGCCATCAGAACTGTGAGC
CAAATAAACCTTTTCTGTATAAATTACCCAAAAAAAAAAAAAAAA
```

*Fig. 1C*

```
  1 GCTTGGTCCCGCCGCCCGGCCGGTGCTCCCTGGCGCAGCCACGCAGGCGCACCGCAGACA   60
    ............................................................
    ............................................................

61 GACCCCTCTGCCATGAACCAGTCCATCCCAGTGGCTCCCACCCCACCCCGCCGCGTGCGG  120
    .............ATGAACCAGTCCATCCCAGTGGCTCCCACCCCACCCCGCCGCGTGCGG   48
    .............-M--N--Q--S--I--P--V--A--P--T--P--P--R--R--V--R-  16

121 CTGAAGCCCTGGCTGGTGGCCCAGGTGAACAGCTGCCAGTACCCAGGGCTTCAATGGGTC  180
 49 CTGAAGCCCTGGCTGGTGGCCCAGGTGAACAGCTGCCAGTACCCAGGGCTTCAATGGGTC  108
 17 -L--K--P--W--L--V--A--Q--V--N--S--C--Q--Y--P--G--L--Q--W--V-   36

181 AACGGGGAAAAGAAATTATTCTGCATCCCCTGGAGGCATGCCACAAGGCATGGTCCCAGC  240
109 AACGGGGAAAAGAAATTATTCTGCATCCCCTGGAGGCATGCCACAAGGCATGGTCCCAGC  168
 37 -N--G--E--K--K--L--F--C--I--P--W--R--H--A--T--R--H--G--P--S-   56

241 CAGGACGGAGATAACACCATCTTCAAGGCCTGGGCCAAGGAGACAGGGAAATACACCGAA  300
169 CAGGACGGAGATAACACCATCTTCAAGGCCTGGGCCAAGGAGACAGGGAAATACACCGAA  228
 57 -Q--D--G--D--N--T--I--F--K--A--W--A--K--E--T--G--K--Y--T--E-   76

301 GGCGTGGATGAAGCCGATCCGGCCAAGTGGAAGGCCAACCTGCGCTGTGCCCTTAACAAG  360
229 GGCGTGGATGAAGCCGATCCGGCCAAGTGGAAGGCCAACCTGCGCTGTGCCCTTAACAAG  288
 77 -G--V--D--E--A--D--P--A--K--W--K--A--N--L--R--C--A--L--N--K-   96

361 AGCCGGGACTTCCGCCTCATCTACGACGGGCCCCGGGACATGCCACCTCAGCCCTACAAG  420
289 AGCCGGGACTTCCGCCTCATCTACGACGGGCCCCGGGACATGCCACCTCAGCCCTACAAG  348
 97 -S--R--D--F--R--L--I--Y--D--G--P--R--D--M--P--P--Q--P--Y--K-  116

421 ATCTACGAGGTCTGCTCCAATGGCCCTGCTCCCACAGACTCCCAGCCCCCTGAGGATTAC  480
349 ATCTACGAGGTCTGCTCCAATGGCCCTGCTCCCACAGACTCCCAGCCCCCTGAGGATTAC  408
117 -I--Y--E--V--C--S--N--G--P--A--P--T--D--S--Q--P--P--E--D--Y-  136

481 TCTTTTGGTGCAGGAGAGGAGGAGGAAGAAGAGGAAGAGCTGCAGAGGATGTTGCCAAGC  540
409 TCTTTTGGTGCAGGAGAGGAGGAGGAAGAAGAGGAAGAGCTGCAGAGGATGTTGCCAAGC  468
137 -S--F--G--A--G--E--E--E--E--E--E--E--L--Q--R--M--L--P--S-  156

541 CTGAGCCTCACAGAGGATGTCAAGTGGCCGCCCACTCTGCAGCCGCCCACTCTGCGGCCG  600
469 CTGAGCCTCACAGAGGATGTCAAGTGGCCGCCCACTCTGCAGCCGCCCACTCTGCGGCCG  528
157 -L--S--L--T--E--D--V--K--W--P--P--T--L--Q--P--P--T--L--R--P-  176

601 CCTACTCTGCAGCCGCCCACTCTGCAGCCGCCCGTGGTGCTGGGTCCCCCTGCTCCAGAC  660
529 CCTACTCTGCAGCCGCCCACTCTGCAGCCGCCCGTGGTGCTGGGTCCCCCTGCTCCAGAC  588
177 -P--T--L--Q--P--P--T--L--Q--P--P--V--V--L--G--P--P--A--P--D-  196

661 CCCAGCCCCCTGGCTCCTCCCCCTGGCAACCCTGCTGGCTTCAGGGAGCTTCTCTCTGAG  720
589 CCCAGCCCCCTGGCTCCTCCCCCTGGCAACCCTGCTGGCTTCAGGGAGCTTCTCTCTGAG  648
197 -P--S--P--L--A--P--P--P--G--N--P--A--G--F--R--E--L--L--S--E-  216

721 GTCCTGGAGCCTGGGCCCCTGCCTGCCAGCCTGCCCCCTGCAGGCGAACAGCTCCTGCCA  780
649 GTCCTGGAGCCTGGGCCCCTGCCTGCCAGCCTGCCCCCTGCAGGCGAACAGCTCCTGCCA  708
217 -V--L--E--P--G--P--L--P--A--S--L--P--P--A--G--E--Q--L--L--P-  236
```

*Fig. 1D-1*

```
 781 GACCTGCTGATCAGCCCCCACATGCTGCCTCTGACCGACCTGGAGATCAAGTTTCAGTAC  840
 709 GACCTGCTGATCAGCCCCCACATGCTGCCTCTGACCGACCTGGAGATCAAGTTTCAGTAC  768
 237 -D--L--L--I--S--P--H--M--L--P--L--T--D--L--E--I--K--F--Q--Y-  256

841 CGGGGGCGGCCACCCCGGGCCCTCACCATCAGCAACCCCCATGGCTGCCGGCTCTTCTAC  900
 769 CGGGGGCGGCCACCCCGGGCCCTCACCATCAGCAACCCCCATGGCTGCCGGCTCTTCTAC  828
 257 -R--G--R--P--P--R--A--L--T--I--S--N--P--H--G--C--R--L--F--Y-  276

901 AGCCAGCTGGAGGCCACCCAGGAGCAGGTGGAACTCTTCGGCCCCATAAGCCTGGAGCAA  960
 829 AGCCAGCTGGAGGCCACCCAGGAGCAGGTGGAACTCTTCGGCCCCATAAGCCTGGAGCAA  888
 277 -S--Q--L--E--A--T--Q--E--Q--V--E--L--F--G--P--I--S--L--E--Q-  296

961 GTGCGCTTCCCCAGCCCTGAGGACATCCCCAGTGACAAGCAGCGCTTCTACACGAACCAG 1020
 889 GTGCGCTTCCCCAGCCCTGAGGACATCCCCAGTGACAAGCAGCGCTTCTACACGAACCAG  948
 297 -V--R--F--P--S--P--E--D--I--P--S--D--K--Q--R--F--Y--T--N--Q-  316

1021 CTGCTGGATGTCCTGGACCGCGGGCTCATCCTCCAGCTACAGGGCCAGGACCTTTATGCC 1080
 949 CTGCTGGATGTCCTGGACCGCGGGCTCATCCTCCAGCTACAGGGCCAGGACCTTTATGCC 1008
 317 -L--L--D--V--L--D--R--G--L--I--L--Q--L--Q--G--Q--D--L--Y--A-  336

1081 ATCCGCCTGTGTCAGTGCAAGGTGTTCTGGAGCGGGCCTTGTGCCTCAGCCCATGACTCA 1140
1009 ATCCGCCTGTGTCAGTGCAAGGTGTTCTGGAGCGGGCCTTGTGCCTCAGCCCATGACTCA 1068
 337 -I--R--L--C--Q--C--K--V--F--W--S--G--P--C--A--S--A--H--D--S-  356

1141 TGCCCCAACCCCATCCAGCGGGAGGTCAAGACCAAGCTTTTCAGCCTGGAGCATTTTCTC 1200
1069 TGCCCCAACCCCATCCAGCGGGAGGTCAAGACCAAGCTTTTCAGCCTGGAGCATTTTCTC 1128
 357 -C--P--N--P--I--Q--R--E--V--K--T--K--L--F--S--L--E--H--F--L-  376

1201 AATGAGCTCATCCTGTTCCAAAAGGGCCAGACCAACACCCCACCACCCTTCGAGATCTTC 1260
1129 AATGAGCTCATCCTGTTCCAAAAGGGCCAGACCAACACCCCACCACCCTTCGAGATCTTC 1188
 377 -N--E--L--I--L--F--Q--K--G--Q--T--N--T--P--P--P--F--E--I--F-  396

1261 TTCTGCTTTGGGGAAGAATGGCCTGACCGCAAACCCCGAGAGAAGAAGCTCATTACTGTA 1320
1189 TTCTGCTTTGGGGAAGAATGGCCTGACCGCAAACCCCGAGAGAAGAAGCTCATTACTGTA 1248
 397 -F--C--F--G--E--E--W--P--D--R--K--P--R--E--K--K--L--I--T--V-  416

1321 CAGGTGGTGCCTGTAGCAGCTCGACTGCTGCTGGAGATGTTCTCAGGGGAGCTATCTTGG 1380
1249 CAGGTGGTGCCTGTAGCAGCTCGACTGCTGCTGGAGATGTTCTCAGGGGAGCTATCTTGG 1308
 417 -Q--V--V--P--V--A--A--R--L--L--L--E--M--F--S--G--E--L--S--W-  436

1381 TCAGCTGATAGTATCCGGCTACAGATCTCAAACCCAGACCTCAAAGACCGCATGGTGGAG 1440
1309 TCAGCTGATAGTATCCGGCTACAGATCTCAAACCCAGACCTCAAAGACCGCATGGTGGAG 1368
 437 -S--A--D--S--I--R--L--Q--I--S--N--P--D--L--K--D--R--M--V--E-  456

1441 CAATTCAAGGAGCTCCATCACATCTGGCAGTCCCAGCAGCGGTTGCAGCCTGTGGCCCAG 1500
1369 CAATTCAAGGAGCTCCATCACATCTGGCAGTCCCAGCAGCGGTTGCAGCCTGTGGCCCAG 1428
 457 -Q--F--K--E--L--H--H--I--W--Q--S--Q--Q--R--L--Q--P--V--A--Q-  476

1501 GCCCTCCTGGAGCAGGCCTTGGTGTTGGCCAGGGGCCCTGGCCTATGCACCCAGCTGGC 1560
1429 GCCCTCCTGGAGCAGGCCTTGGTGTTGGCCAGGGGCCCTGGCCTATGCACCCAGCTGGC 1488
 477 -A--P--P--G--A--G--L--G--V--G--Q--G--P--W--P--M--H--P--A--G-  496
```

*Fig. 1D-2*

```
1561 ATGCAATAACAAGGCTGCAGACGGTGACTGGCCCTGGCTTCCTGGGTGGCGGTGCGGACT 1620
1489 ATGCAATAA................................................... 1497
 497 -M--Q--*-.................................................   498

1621 GATGTGGAGATGTGACAGCCCCGATGAGCACCTGGCTGGCTGCAGGGTCCTACCTCTGGG 1680

1681 TTTCCTGGAAGTGGATTTGGGCCAAGAAGGAGAGGGAGAAAGGCCCGAGCCCCTGCCTTC 1740

1741 CCGGGCCTTTCTCTCCTGGGCTGTCTCTGGTCTGGTCAGCCTGGCTCTCGGGAAATTCAG 1800

1801 CCATGAGCAGGGAAAGAACTCTCCCAACCCTGGGGCCTAGCTGTATAGGAGGAATTGCCT 1860

1861 AAGGGTGGCCCACTCTTGTGATTGCCCCATTTCCTCTGGCAACAAAAGCCAGAGTGTTGT 1920

1921 GGGCCAAGTCCCCCCACAGGGCCTCTGCAGGGCATGGCCCTGATTTCCCTGGTTTGAGAC 1980

1981 TCACTTCCTCATCTCCCTGTCCTCTGAGATAATATGAGTGAGCACTTAGGTATCATATCA 2040

2041 GATGCTCAAGGCTGGCAGCTACCCCCTTCTTGAGAGTCCAAGAACCTGGAGCAGAAATAA 2100

2101 TTTTTATGTATTTTTGGATTAATGAATGTTAAAAACAGACTCAGCTGTTTCTTTCCTTTT 2160

2161 ACTACTACCAGTTGCTCCCATGCTGCTCCACCAGGCCCTGTTTCGGATGCCAACTGGCCC 2220

2221 ACTCCCCAAGCACTTGCCCCAGCTTGCGACCATTGGCACTGGGAGGGCCTGGCTTCTGG 2280

2281 GCTGATGGGTCAGTTGGGCCTTCATAAACACTCACCTGGCTGGCTTTGCCTTCCAGGAGG 2340
```

*Fig. 1D-3*

```
2341 AAGCTGGCTGAAGCAAGGGTGTGGAATTTTAAATGTGTGCACAGTCTGGAAAACTGTCAG 2400
     ............................................................
     ............................................................

2401 AATCAGTTTTCCCATAAAAGGGTGGGCTAGCATTGCAGCTGCATTTGGGACCATTCAAAT 2460
     ............................................................
     ............................................................

2461 CTGTCACTCTCTTGTGTATATTCCTGTGCTATTAAATATATCAGGGCAGTGCATGTAAAT 2520
     ............................................................
     ............................................................

2521 CATCCTGATATATTTAATATATTTATTATATTGTCCCCCGAGGTGGGGACAGTGAGTGAG 2580
     ............................................................
     ............................................................

2581 TTCTCTTAGTCCCCCCAGAGCTGGTTGTTAAAGAGCCTGGCACCTACCCGCTCTCACTTC 2640
     ............................................................
     ............................................................

2641 ATCTGTGTCATCTCTGCACACTCCAGCCCACTTTCTGCCTTCAGCCATTGAGTGGAAGCT 2700
     ............................................................
     ............................................................

2701 GCCCCAGGCCCTTACCAGGTGCAGATGCCCAATCTTGATGCCCAGCCATCAGAACTGTGA 2760
     ............................................................
     ............................................................

2761 GCCAAATAAACCTTTTTCTGTATAAA                                    2786
     ..........................
     ..........................
```

*Fig. 1D-4*

DOSAGE FORM FOR TREATING SEVERE ASTHMA

CROSS REFERENCE TO RELATED APPLICATIONS

This application is a continuation of U.S. patent application Ser. No. 16/539,383, filed Aug. 13, 2019, which is a divisional application of U.S. patent application Ser. No. 15/903,505, filed Feb. 23, 2018, which claims the benefit of U.S. Provisional Patent Application No. 62/463,243, filed Feb. 24, 2017, each of which is incorporated herein by reference in its entirety.

STATEMENT REGARDING FEDERAL FUNDING

This invention was made with government support under Grant No. HL113956 awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 1904911_ST25.txt. The size of the text file is 24,276 bytes, and the text file was created on Aug. 7, 2019.

Asthma is a highly prevalent condition of immune dysfunction affecting approximately 25 million American adults and children in the United States according to the Centers for Disease Control and Prevention. Of these, approximately 90% exhibit a relatively mild form of the condition, which importantly is treatable at a considerable rate of success in most cases. However, the remaining 5-10% of asthmatics are classified as having severe disease and in these instances, not only is there increased morbidity and mortality, but also a general poor response to corticosteroids, which constitute the mainstay of asthma therapy.

The primary reason that severe asthma presents as a unique clinical entity, and therefore does not respond to standard therapy, is that differential immunological processes appear to be operative compared to mild/moderate asthma conditions. Specifically, high expression of the type 1 cytokine IFN-γ is observed in ~50% of severe asthmatics which is a notable departure from the type 2 immune pathway commonly found in the mild/moderate disease (Raundhal, M., et al. High IFN-gamma and low SLPI mark severe asthma in mice and humans. *J Clin Invest.* Aug. 3 2015; 125(8):3037-3050).

Although severe asthma comprises only 5-10% of all asthma, the economic impact of severe asthma is 40-50% of the total healthcare cost of all asthma which is $56 billion in the United States as estimated by the World Health Organization. This is because of more frequent emergency care and hospitalization needed for these subjects along with greater expenditure for medications. Another layer of complexity in successfully treating severe asthmatics is the heterogeneity in immune response in these patients. Therefore, novel therapeutic approaches to addressing severe asthma are direly needed.

SUMMARY

Provided herein is a method of treating asthma in a patient, including the step of reducing IRF5 activity to a level effective to treat one or more symptoms of asthma in a patient.

Also provided herein is a composition including a corticosteroid and an interfering nucleic acid, such as a miRNA or an siRNA, or an interfering RNA able to down-regulate expression of IRF5 in a patient.

BRIEF DESCRIPTION OF THE DRAWINGS

FIGS. 1A though 1D-4 provide exemplary amino acid (1A (SEQ ID NO: 1) and 1B (SEQ ID NO: 2)) and mRNA (1C (SEQ ID NO: 3) and 1D-1 through 1D-4 (top row—SEQ ID NO: 4; middle row—SEQ ID NO: 5; and bottom row—SEQ ID NO: 6)) sequences for human IRF5.

DETAILED DESCRIPTION

Figure 2:
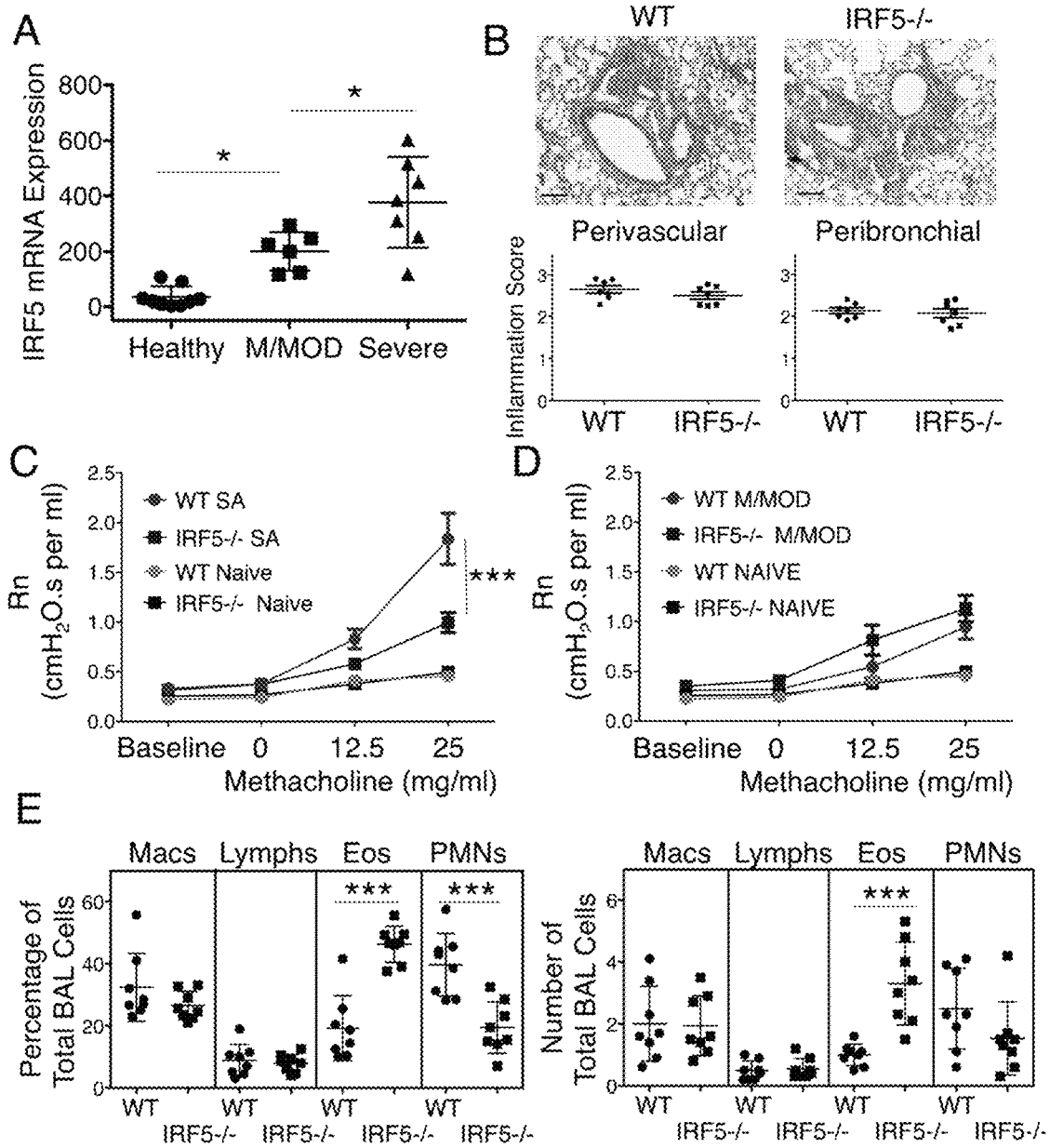
FIG. 2 shows IRF5 expression in human severe asthma, and airway hyperresponsiveness in IRF5$^{-/-}$ mice. Panel A shows human bronchoalveolar lavage (BAL) cells were obtained from human subjects undergoing bronchoscopy. Subjects were clinically classified as healthy controls, mild to moderate asthmatics (M/MOD), or severe asthmatics. qRT-PCR was performed on total BAL cell mRNA for IRF5 expression (n=7 severe, 6 mild/moderate, 10 healthy controls). Panels B-E show wild type or IRF5$^{-/-}$ mice were subjected to a model of (panels B,C,E) severe asthma (SA) or (panel D) mild to moderate asthma. (Panel B) PAS stains of lung sections along with inflammation scores in the perivascular and peribronchial regions. Scale bar 100 μm (n=7 per group). (Panel C) Airway hyperresponsiveness (AHR) expressed as Rn (Newtonian resistance or central airway resistance) in the severe asthma model. (Panel D) AHR in the mild to moderate model. (Panel E) Cytospins of total BAL cells were prepared for differential cell counting. A total of at least 300 cells were counted and the results shown are expressed as percentage of the total (left-hand panel) and the calculated number of cells recovered (right-hand panel) (Macs, macrophages; Lymphs, lymphocytes, Eos, eosinophils, PMNs, neutrophils). *$P \leq 0.05$, ***$P \leq 0.001$ Kruskal-Wallis with Dunn's multiple comparison test. n=8 mice per group (C-E). Data are mean±SEM and are representative of 3 independent experiments.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts.

As used herein, the term "patient" or "subject" refers to members of the animal kingdom including but not limited to human beings and "mammal" refers to all mammals, including, but not limited to human beings.

As used herein, the "treatment" or "treating" asthma, such as corticosteroid-insensitive asthma, severe asthma, or asthma in a patient displaying (exhibiting, having, etc.) a Th1, optionally a Th1/Th17$^{hi}$Th2$^{lo}$, immune profile, means administration to a patient by any suitable dosage regimen, procedure and/or administration route of a composition, device or structure with the object of achieving a desirable clinical/medical end-point, including but not limited to, reduction of asthma symptoms, including lessening of respiratory inflammation and improvement in respiration parameters, such as peak expiratory flow.

Drug products, or pharmaceutical compositions comprising an active agent (e.g., drug), for example, an active agent that decreases Interferon regulatory factor 5 (IRF5) activity, may be prepared by any method known in the art of pharmacy, for example, by bringing into association the active ingredient with the carrier(s) or excipient(s). As used herein, a "pharmaceutically acceptable excipient", "carrier" or "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable excipients include one or more of water, saline, phosphate buffered saline, dextrose, glycerol, ethanol and the like, as well as combinations thereof. In many cases, it may be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the active agent. In certain aspects, the active compound may be prepared with a carrier that will protect the compound against rapid release, such as a controlled release formulation, including implants, transdermal patches, and microencapsulated delivery systems. Biodegradable, biocompatible polymers can be used in delivery systems, such as ethylene vinyl acetate, polyanhydrides, polyglycolic acid, collagen, polyorthoesters, and polylactic acid. Many methods for the preparation of such formulations are broadly-known to those skilled in the art.

Additionally, active agent-containing compositions may be in variety of forms. The preferred form depends on the intended mode of administration and therapeutic application, which will in turn dictate the types of carriers/excipients. Suitable forms include, but are not limited to, liquid, semi-solid and solid dosage forms.

Pharmaceutical formulations adapted for oral administration may be presented, for example and without limitation, as discrete units such as capsules or tablets; powders or granules; solutions or suspensions in aqueous or non-aqueous liquids; edible foams or whips; or oil-in-water liquid emulsions or water-in-oil liquid emulsions. In certain embodiments, the active agent may be contained in a formulation such that it is suitable for oral administration, for example, by combining the active agent with an inert diluent or an assimilable edible carrier. The active agent (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Pharmaceutical formulations adapted for transdermal administration may be presented, for example and without limitation, as discrete patches intended to remain in intimate contact with the epidermis of the recipient for a prolonged period of time or electrodes for iontophoretic delivery.

Pharmaceutical formulations adapted for topical administration may be formulated, for example and without limitation, as ointments, creams, suspensions, lotions, powders, solutions, pastes, gels, sprays, aerosols or oils.

Pharmaceutical formulations adapted for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include, without limitation, fine particle dusts or mists which may be generated by means of various types of metered dose pressurized aerosols, nebulizers or insufflators. In the context of delivery of the active agents described herein for treatment of asthma, inhalation drug products, such as metered-dose inhalers, as are broadly-known in the pharmaceutical arts, are used. Metered dose inhalers are configured to deliver a single dose of an active agent per actuation, though multiple actuations may be needed to effectively treat a given patient.

Pharmaceutical formulations adapted for parenteral administration include aqueous and non-aqueous sterile injection solutions which may contain, for example and without limitation, anti-oxidants, buffers, bacteriostats, lipids, liposomes, emulsifiers, also suspending agents and rheology modifiers. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets.

Therapeutic compositions typically must be sterile and stable under the conditions of manufacture and storage. For example, sterile injectable solutions can be prepared by incorporating the active agent in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A "therapeutically effective amount" refers to an amount of a drug product or active agent effective, at dosages and for periods of time necessary, to achieve the desired therapeutic result, such as, in the case of asthma, reduction of inflammation and/or improvement of respiration, e.g., peak flow. An "amount effective" for treatment of a condition is an amount of an active agent or dosage form, such as a single or multiple metered doses from a metered-dose inhaler, effective to achieve a determinable end-point. The "amount effective" is preferably safe—at least to the extent the benefits of treatment outweighs the detriments and/or the detriments are acceptable to one of ordinary skill and/or to an appropriate regulatory agency, such as the U.S. Food and Drug Administration. A therapeutically effective amount of an active agent may vary according to factors such as the disease state, age, sex, and weight of the individual, and the ability of the active agent to elicit a desired response in the individual. A therapeutically effective amount is also one in which any toxic or detrimental effects of the active agent are outweighed by the therapeutically beneficial effects. A "prophylactically effective amount" refers to an amount effective, at dosages and for periods of time necessary, to achieve a desired prophylactic result. Typically, since a prophylactic dose is used in subjects prior to or at an earlier stage of disease, the prophylactically effective amount may be less than the therapeutically effective amount.

Dosage regimens may be adjusted to provide the optimum desired response (e.g., a therapeutic or prophylactic response). For example, a single bolus may be administered, several divided doses may be administered over time, or the composition may be administered continuously or in a pulsed fashion with doses or partial doses being administered at regular intervals, for example, ever 10, 15, 20, 30, 45, 60, 90, or 120 minutes, every 2 through 12 hours daily, or every other day, etc. be proportionally reduced or increased as indicated by the exigencies of the therapeutic situation. In some instances, it may be especially advantageous to formulate parenteral or inhaled compositions in dosage unit form for ease of administration and uniformity of dosage. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

IRF5 activity can be decreased by a number of methods, including, without limitation: antisense methods, RNA interference methods, use of binding reagents specific to the IRF5 gene product, use of IRF5 binding sequence decoys comprising a nucleic acid comprising an IRF5 nucleotide-binding sequence motif acting to competitively bind IRF5, ribozyme methods, or by use of small-molecule or other therapeutic agents able to decrease IRF5 activity. Non-viral gene transfer methods also are well-known, and include liposome technologies (see, e.g., Claudia Zylberberg, C., et al. Pharmaceutical liposomal drug delivery: a review of new delivery systems and a look at the regulatory landscape, Drug Delivery (2016) 23:9, 3319-3329).

A "binding reagent" is a reagent, compound or composition able to specifically bind a target compound, such as IRF5. Binding reagents include, without limitation, antibodies (polyclonal, monoclonal, humanized, etc.), antibody fragments (e.g., a recombinant scFv), antibody mimetics such as affibodies, affilins, affimers, affitins, alphabodies, anticalins, avimers, DARPins, fynomers, monobodies, nucleic acid ligands (e.g., aptamers), engineered proteins, antigens, epitopes, haptens, or any target-specific binding reagent. In aspects, binding reagents includes as a class: monoclonal antibodies, or derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, multivalent versions of the foregoing, and any paratope-containing compound or composition; multivalent activators including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; nucleic acids and analogs thereof that bind a target compound; or receptor molecules which naturally interact with a desired target molecule.

By "target-specific" or reference to the ability of one compound to bind another target compound specifically, it is meant that the compound binds to the target compound to the exclusion of others in a given reaction system, e.g., in vitro, or in vivo, to acceptable tolerances, permitting a sufficiently specific diagnostic or therapeutic effect according to the standards of a person of skill in the art, a medical community, and/or a regulatory authority, such as the U.S. Food and Drug Agency (FDA). In aspects, in the context of targeting IRF5, and down-regulating IRF5 activity, binding IRF5 to safely and effectively treat an asthmatic condition as described herein.

A "gene" is a sequence of DNA or RNA which codes for a molecule, such as a protein or a functional RNA that has a function. Nucleic acids are biopolymers, or small biomolecules, essential to all known forms of life. They are composed of nucleotides, which are monomers made of three components: a 5-carbon sugar, a phosphate group and a nitrogenous base. If the sugar is a simple ribose, the polymer is RNA; if the sugar is derived from ribose as deoxyribose, the polymer is DNA. DNA uses the nitrogenous bases guanine, thymine, adenine, and cytosine. RNA uses the nitrogenous bases guanine, uracil, adenine, and cytosine.

Complementary refers to the ability of polynucleotides (nucleic acids) to hybridize to one another, forming interstrand base pairs. Base pairs are formed by hydrogen bonding between nucleotide units in antiparallel polynucleotide strands. Complementary polynucleotide strands can base pair (hybridize) in the Watson-Crick manner (e.g., A to T, A to U, C to G), or in any other manner that allows for the formation of duplexes. When using RNA as opposed to DNA, uracil rather than thymine is the base that is considered to be complementary to adenosine. Two sequences comprising complementary sequences can hybridize if they form duplexes under specified conditions, such as in water, saline (e.g., normal saline, or 0.9% w/v saline) or phosphate-buffered saline), or under other stringency conditions, such as, for example and without limitation, 0.1×SSC (saline sodium citrate) to 10×SSC, where 1×SSC is 0.15M NaCl and 0.015M sodium citrate in water. Hybridization of complementary sequences is dictated, e.g., by salt concentration and temperature, with the melting temperature (Tm) lowering with increased mismatches and increased stringency. Perfectly matched sequences are said to be fully complementary, or have 100% sequence identity (gaps are not counted and the measurement is in relation to the shorter of the two sequences). In one aspect, a sequence that "specifically hybridizes" to another sequence, does so in a hybridization solution containing 0.5M sodium phosphate buffer, pH 7.2, containing 7% SDS, 1 mM EDTA, and 100 mg/ml of salmon sperm DNA at 65° C. for 16 hours and washing twice at 65° C. for twenty minutes in a washing solution containing 0.5×SSC and 0.1% SDS, or does so under conditions more stringent than 2×SSC at 65° C., for example, in 0.2×SSC at 55° C. A sequence that specifically hybridizes to another typically has at least 80%, 85%, 90%, 95%, OR 99% sequence identity with the other sequence.

A "gene" is a sequence of DNA or RNA which codes for a molecule, such as a protein or a functional RNA that has a function. Nucleic acids are biopolymers, or small biomolecules, essential to all known forms of life. They are composed of nucleotides, which are monomers made of three components: a 5-carbon sugar, a phosphate group and a nitrogenous base. If the sugar is a simple ribose, the polymer is RNA; if the sugar is derived from ribose as deoxyribose, the polymer is DNA. DNA uses the nitrogenous bases guanine, thymine, adenine, and cytosine. RNA uses the nitrogenous bases guanine, uracil, adenine, and cytosine.

Gene expression is the process by which information from a gene is used in the synthesis of a functional gene product, e.g., a protein or functional RNA. Gene expression involves various steps, including transcription, translation, and post-translational modification of a protein.

Transcription is the process by which the DNA gene sequence is transcribed into pre-mRNA (messenger RNA). The steps include: RNA polymerase, together with one or more general transcription factors, binds to promoter DNA. Transcription factors (TFs) are proteins that control the rate of transcription of genetic information from DNA to messenger RNA, by binding to a specific DNA sequence (i.e., the promoter region). The function of TFs is to regulate genes in order to make sure that they are expressed in the right cell at the right time and in the right amount throughout the life of the cell and the organism. The promoter region of a gene is a region of DNA that initiates transcription of that particular gene. Promoters are located near the transcription start sites of genes, on the same strand, and often, but not exclusively, are upstream (towards the 5' region of the sense strand) on the DNA. Promoters can be about 100-1000 base pairs long. Additional sequences and non-coding elements can affect transcription rates. If the cell has a nucleus (eukaryotes), the RNA is further processed. This includes polyadenylation, capping, and splicing. Polyadenylation is the addition of a poly(A) tail to a messenger RNA. The poly(A) tail consists of multiple adenosine monophosphates; in other words, it is a stretch of RNA that has only adenine bases. In eukaryotes, polyadenylation is part of the process that produces mature messenger RNA (mRNA) for translation. Capping refers to the process wherein the 5' end of the pre-mRNA has a specially altered nucleotide. In eukaryotes, the 5' cap (cap-0), found on the 5' end of an mRNA molecule, consists of a guanine nucleotide connected to mRNA via an unusual 5' to 5' triphosphate linkage. During RNA splicing, pre-mRNA is edited. Specifically, during this process introns are removed and exons are joined together. The resultant product is known as mature mRNA. The RNA may remain in the nucleus or exit to the cytoplasm through the nuclear pore complex.

RNA levels in a cell, e.g., mRNA levels, can be controlled post-transcriptionally. Native mechanisms, including: endogenous gene silencing mechanisms, interference with translational mechanisms, interference with RNA splicing mechanisms, and destruction of duplexed RNA by RNAse H, or RNAse H-like, activity. As is broadly-recognized by those of ordinary skill in the art, these endogenous mechanisms can be exploited to decrease or silence mRNA activity in a cell or organism in a sequence-specific, targeted manner. Antisense technology typically involves administration of a single-stranded antisense oligonucleotide (ASO) that is chemically-modified, e.g., as described herein, for bio-stability, and is administered in sufficient amounts to effectively penetrate the cell and bind in sufficient quantities to target mRNAs in cells. RNA interference (RNAi) harnesses an endogenous and catalytic gene silencing mechanism, which means that once, e.g., a microRNA, or double-stranded siRNA has been delivered, either by conjugation or in nanoparticles into the cytosol, they are efficiently recognized and stably incorporated into the RNA-induced silencing complex (RiSC) to achieve prolonged gene silencing. Both antisense technologies and RNAi have their strengths and weaknesses, either may be used effectively to decrease or silence expression of a gene, such as IRF5 (see, e.g., Watts, J. K., et al. Gene silencing by siRNAs and antisense oligonucleotides in the laboratory and the clinic (2012) 226(2): 365-379).

During translation, mRNA is decoded in a ribosome, outside the nucleus, to produce a specific amino acid chain, or polypeptide. A codon refers to a sequence of three nucleotides. The information for protein synthesis is the form of these three-nucleotide codons, which each specify one amino acid. The protein coding regions of each mRNA is composed of a contiguous, non-overlapping string of codons called an open-reading frame (ORF). Each ORF specifies a single protein and starts and ends at internal sites within the mRNA. That is, the ends of an ORF are distinct from the ends of the mRNA. Translation starts at the 5' end of the ORF and proceeds one codon at a time to the 3' end. The first and last codons of an ORF are known as the start and stop codons. Polycistronic mRNAs are mRNAs containing multiple ORFs, and those mRNAs encoding a single ORF are known as monocistronic mRNAs.

Translation proceeds in three phases: initiation, elongation and termination. For translation to occur, the ribosome must be recruited to the mRNA. To facilitate binding by a ribosome, many prokaryotic ORFs contain a short sequence upstream of the start codon called the ribosome binding site (RBS), also known as the Shine-Dalargarno sequence. This area of the mRNA that is upstream of the start codon is known as the 5' untranslated region (UTR), this region is also known as a leader sequence or leader RNA. In eukaryotes, 5' cap assists in ribosome binding during translation, among other roles. Additionally, the presence of a Kozak sequence (a purine three bases upstream of the start codon and a guanine immediately downstream) helps increase the efficiency of translation. During elongation, the ribosome catalyzes sequential additions of aminoacyl-tRNA corresponding to codons of the ORF of the mRNA, and transfers amino acids to the nascent polypeptide, based on the sequence of codons. The ribosome then moves to the next mRNA codon to continue the process, creating an amino acid chain. In termination of translation, a stop codon is reached, at which point, translation ceases. The nascent polypeptide can then be post-translationally modified, wherein chemical modifications are added, e.g., to the C- or N-termini of the polypeptide.

As used herein, "reagent" when used in the context of an antisense, RNAi, or ribozyme, or other single-stranded or double-stranded RNA interfering nucleic acids, refers not only to RNA structures, but effective nucleic acid analog structures. In antisense and RNAi technologies, use of RNA poses significant delivery issues due to the lability of RNA molecules. As such, RNA is commonly chemically-modified to produce nucleic acid analogs, not only to enhance stability of the nucleic acid molecules, but often resulting in increased binding affinity, and with reduced toxicity. Such modifications are broadly-known to those of ordinary skill in the art, and are available commercially (see, e.g., Corey, D. R., Chemical modification: the key to clinical application of RNA interference? (2007) J Clin Invest.117(12):3615-3622, also describing RNAi, and United States Patent Publication No. 20170081667). Non-limiting examples of modifications to the nucleic acid structure in nucleic acid analogs include: modifications to the phosphate linkage, such as phosphoramidates or phosphorothioates; sugar modification, such as 2'-O, 4'-C methylene bridged, locked nucleic acid (LNA), 2'-methoxy, 2'-O-methoxyethyl (MOE), 2'-fluoro, S-constrained-ethyl (cEt), and tricyclo-DNA (tc-DNA); and non-ribose structures, such as phosphorodiamidate morpholino (PMO) and peptide-nucleic acids (PNA).

In addition to those IRF5-active reagents described herein, antisense reagents (ASOs), RNAi reagents, ribozyme reagents, and other nucleic acid-based methods of reducing gene expression, can be designed and tested based on known sequences of IRF5 RNA and gene structure (exemplary sequences are provided herein and are broadly-available, and the IRF5 gene is well-studied), and can be designed and/or obtained from a number of commercial sources, for example, readily available commercial tools, such as the siRNA Wizard™ (InvivoGen) or the siDESIGN Center (GE Dharmacon), or by genetic editing, e.g., by CRISPR/Cas9 editing or other gene editing methods. Based on the present disclosure, one of ordinary skill can readily obtain, design, and/or produce an active agent capable of decreasing IRF5 activity.

Therefore, according to one aspect, provided herein is a method of treating asthma in a patient, comprising reducing IRF5 activity to a level effective to treat one or more symptoms of asthma in a patient. By "reducing activity" of a gene or gene product, e.g., IFR5, it is meant, by any method decreasing, suppressing, or silencing expression of the gene, decreasing activity of the gene product, and/or reducing available levels of the gene product in the patient. Activity of IRF5 can be reduced, e.g., by use of antisense nucleic acids, or by use of RNAi reagents. Activity of IRF5 also can be reduced, e.g., by antagonism, or otherwise blocking or interfering with the activity of IRF5, or by mutation. Available levels of the gene product can be reduced in a patient, for example, either systemically or locally in the respiratory tract, e.g., by binding of the IRF5 with an IRF5-binding reagent, such as an antibody, and antibody fragment, or an anti-IRF5 paratope-containing polypeptide compositions, or a nucleic acid decoy comprising an IRF5 nucleotide binding sequence motif acting to competitively bind IRF5.

In aspects, the asthma is corticosteroid-insensitive, which also is referred to as steroid resistant asthma or steroid-refractory asthma, referring to asthma that responds poorly to corticosteroids, or the patient needs such high doses to control the disease that side-effects become a serious problem. In aspects, the patient displays a Th1 immune profile, optionally a Th1/Th17$^{hi}$Th2$^{lo}$, immune profile.

In aspects, a composition is provided, such as an inhaled dosage form, for treatment of asthma, such as corticosteroid-refractory, or severe asthma, comprising a corticosteroid and an ASO or interfering nucleic acid able to decrease IRF5 activity, and/or down-regulate or silence expression of IRF5 in a patient.

IRF5 is a protein that in humans is encoded by the IRF5 gene. It is a member of the interferon regulatory factor (IRF) family, a group of transcription factors with diverse roles, including virus-mediated activation of interferon, and modulation of cell growth, differentiation, apoptosis, and immune system activity. Members of the IRF family are characterized by a conserved N-terminal DNA-binding domain containing tryptophan (W) repeats. IRF5 requires phosphorylation of carboxyl-terminal serines for the nuclear localization and transactivation.

IRF5 exists as multiple isoforms that are expressed in a cell type-specific manner. It encodes a 60-63-kDa polypeptide (see, e.g., Mancl, M. E., et al., Two Discrete Promoters Regulate the Alternatively Spliced Human Interferon Regulatory Factor-5 Isoforms MULTIPLE ISOFORMS WITH DISTINCT CELL TYPE-SPECIFIC EXPRESSION, LOCALIZATION, REGULATION, AND FUNCTION (2005) J. Biol.

Chem. 280(22):21078-21090; OMIM 607218, HGNC 6120, GenBank NM_001098627.3(transcript variant 3); Ensembl Gene: IRF5 ENSG00000128604, NG_012306, *Homo sapiens* interferon regulatory factor 5 (IRF5), RefSeqGene on chromosome 7). Table 1 provides reference information for 15 transcript variants of IRF5.

TABLE 1

| Name* | Transcript ID* | Bp | Protein | GenBank RefSeq |
|---|---|---|---|---|
| IRF5-213 | ENST00000489702.6 | 2988 | 514aa | Protein coding | NM_001347928 NP_001334857 |
| IRF5-203 | ENST00000402030.6 | 2786 | 498aa | Protein coding | NM_001098630 NP_001092100 |
| IRF5-201 | ENST00000249375.8 | 2749 | 498aa | Protein coding | NM_032643 NP_116032 |
| IRF5-208 | ENST00000473745.5 | 2282 | 498aa | Protein coding | NM_001098627 NP_001092097 |
| IRF5-202 | ENST00000357234.9 | 1680 | 514aa | Protein coding | NM_001098629 NP_001092099 |
| IRF5-210 | ENST00000477535.5 | 1374 | 412aa | Protein coding | NM_001242452 NP_001229381 |
| IRF5-215 | ENST00000619830.1 | 1652 | 147aa | Protein coding | — |
| IRF5-211 | ENST00000479582.5 | 637 | 141aa | Protein coding | — |
| IRF5-214 | ENST00000613821.4 | 595 | 157aa | Protein coding | — |
| IRF5-207 | ENST00000467002.1 | 560 | 59aa | Protein coding | — |
| IRF5-205 | ENST00000464557.5 | 553 | 106aa | Protein coding | — |
| IRF5-206 | ENST00000465603.5 | 2088 | 147aa | Nonsense mediated decay | — |
| IRF5-209 | ENST00000473787.5 | 587 | 104aa | Nonsense mediated decay | — |
| IRF5-204 | ENST00000461416.1 | 1057 | N/A | Retained intron | — |
| IRF5-212 | ENST00000488569.5 | 923 | N/A | | |

*e!Ensembl (east) designations (from Transcript: IRF5-213 ENST00000489702.6), Ensembl release 91-December 2017

FIGS. 1A and 1B provide exemplary amino acid sequence for human IRF5 (FIG. 1A: NP_116032, interferon regulatory factor 5 isoform b [*Homo sapiens*] and FIG. 1B: AAA96056, interferon regulatory factor 5 [*Homo sapiens*]). FIG. 1C provides an exemplary mRNA sequence for human IRF5 (GenBank Reference No. NM_032643). FIGS. 1D-1 through 1D-4 show additional exemplary IRF5 mRNA and protein sequences (ENSEMBL cDNA: IRF5-001 ENST00000402030.6), showing sequence variations.

In aspects, by "decreasing IRF5 activity" or "downregulating IRF5 activity", it is meant any action that results in lower activity of IRF5 in a cell or patient—typically by use of a therapeutic agent. Useful therapeutic agents include, without limitation, antisense or RNAi compositions; binding reagents, such as antibodies (including antibody fragments or antibody-based polypeptide ligands), and aptamers; antagonists; decoys; and peptide-based therapies.

For example, United States Patent Application Publication No. 2017/0081667, incorporated herein by reference for its disclosure of hundreds of candidate IRF5-regulating nucleic acids and for its summary of RNA suppression methods, discloses a large number of therapeutic nucleic acid oligomers that downregulate or decrease IRF5 activity, including, without limitation:

5'-gaagaagcucauuacuguacaggnn-3' (SEQ ID NO: 7), and

5'-caccuguacaguaaugagcuucuucuc-3' (SEQ ID NO: 8), and sequences complementary to either.

United States Patent Application Publication No. 2016/0009772 discloses cell penetrating peptides that bind IRF5, such as a peptide comprising an amino acid sequence of 20-40 amino acids, comprising, in part, an amino acid sequence motif selected from the group consisting of:

a) Y-R1-R2-R3-L-R4-R5-V (SEQ ID NO: 9), wherein
   Y is tyrosine,
   R1 is an amino acid selected from the group of tryptophan (W) or alanine (A),
   R2 is an amino acid selected from the group consisting of leucine (L) or threonine (T),
   R3 is an amino acid selected from the group consisting of leucine (L), alanine (A), aspartic acid (D), or phenylalanine (F), L is leucine,
   R4 is an amino acid selected from the group consisting of leucine (L), glycine (G) or threonine (T),
   R5 is an amino acid selected from the group consisting of phenylalanine (F), leucine (L) or methionine (M), and
   V is valine; or b) K-D-R6-M-V-R7-F-K-D (SEQ ID NO: 10), wherein
   K is lysine,
   D is aspartic acid,
   R6 is an amino acid selected from the group consisting of leucine or aspartic acid,
   M is methionine,
   R7 is selected from the group consisting of Glutamine-Tryptophan (Q-W) and arginine-phenylalanine (R-F), and
   F is phenylalanine;

or a pharmaceutically acceptable salt thereof.

United States Patent Application Publication No. 2014/0030218 discloses treatments of autoimmune disease other than allergy or asthma with therapeutically effective amounts of an inhibitor of IRF5, including as candidate classes of compounds: competitive inhibitor peptides of IRF5, IRF4, macrophage colony stimulating factor (M-CSF) and M-CSF receptor agonists, RNAi, antisense, and ribozyme reagents, and describing various modes of inhibition of IRF5 and transcriptional variants thereof, such as inhibition of binding of IRF5 to its DNA binding site, or to its binding partners, such as RelA, MyD88, TRAF6, or TRIM28.

In Courties, G., et al. (In Vivo Silencing of the Transcription Factor IRF5 Reprograms the Macrophage Phenotype and Improves Infarct Healing, *J. Am. Coll. Cardiol.* 2104; 63:1556-66), twenty-four IRF5 siRNA sequences were tested, with two having, of those tested, the strongest in vitro silencing activity on IRF5, and exhibiting in vivo effect, increasing myocardial infarct healing, and influencing macrophage polarization in injured tissue. This article illustrates methods of testing efficacy of RNAi reagents, the efficacy of RNAi reagents in vivo, and the ability of designed IRF5 RNAi reagents to effectively decrease, e.g., silence, IRF5 expression.

In Raundhal, M., et al. *J Clin Invest. Aug.* 3 2015; 125(8):3037-3050, the development of a novel murine model system that manifests high IFN-γ expression and mimics the essential aspects of human severe asthma is reported along with the finding that IFN-γ is essential for airway hyperresponsiveness (AHR) in response to perturbation as occurs in humans resulting in the aforementioned morbidity. The animal model has thus become a powerful tool for investigating specific immunologic mechanisms that result in severe asthma pathology. Here, a novel interventional pathway involving IRF5 is described. IRF5 is seen to be elevated in the lungs of severe asthmatics compared to their mild/moderate or healthy control counterparts. IRF5 expression in dendritic cells (DCs), which prime and perpetuate specific immune responses, is shown to regulate interleukin 12 (IL-12), a cytokine long-known to be indispensable for type 1 immune response i.e., T cell production of IFN-γ. Data show that in IRF5-deficient mice, expression of IL-12 and subsequently IFN-γ is significantly reduced leading to greatly diminished morbidity in terms of AHR. This phenomenon was observed not only during the initiation of an immune response, but also during ongoing airway inflammation mimicking the chronic inflammatory process that is asthma. Thus, intervention is aimed at specifically blocking IRF5 function in the lungs of severe asthmatics, and represents a highly promising modality to bring treatment to individuals who essentially have none, and in the process, potentially reduce the associated profound and detrimental economic impact.

Example 1

As described above, severe asthma (SA) is a significant problem both clinically and economically given its poor response to corticosteroids (CS), which is the mainstay of asthma therapy. While type 2 immune response is a feature of milder CS-responsive allergic asthma, a more complex type 1 (IFN-γ)-dominated immune response is present in >50% of severe asthmatics despite high dose CS treatment. Also, IFN-γ was observed to be central to increased airway hyperreactivity (AHR). The transcription factor IRF5 expressed in M1 macrophages can induce a Th1/Th17 response in co-cultured human T cells. As is shown below, higher expression of IRF5 is observed in bronchoalveolar lavage (BAL) cells of severe asthmatics as compared to that in cells from milder asthmatics or healthy controls. In the model of severe asthma, IRF5$^{-/-}$ mice mounted significantly lower AHR compared to WT mice, although CS failed to reduce AHR in WT mice. CD4$^+$ T cells primed by IRF5-deficient DCs display a severe limitation in IFN-γ production during both primary and secondary stimulations. This study highlights IRF5 as a target for therapeutic intervention in CS-refractory human severe asthma with a strong Th1 immune component.

Methods

Human BAL cells. Human subjects were recruited as part of the Severe Asthma Research Program (SARP) and bronchoscopy to obtain bronchoalveolar lavage (BAL) cells was performed according to previously published guidelines and procedures. Each subject was categorized as severe asthmatic, mild/moderate asthmatic, or healthy control based upon the latest European Respiratory Society/American Thoracic Society (ERS/ATS) criteria. Total BAL cell mRNA was isolated (RNeasy Kit; QIQGEN) from samples that had been immediately placed in RLT buffer (QIAGEN) and qRT-PCR was performed as described below using a human primer and probe set (Hs00158114_ml; Life Technologies).

Mice. IRF5-deficient mice (originally derived by Dr. T. Mak at the University of Toronto and provided to us by Dr. I. Rifkin at Boston University) on C57BL/6J background. These mice were determined, before transfer to the University of Pittsburgh, to be free of the DOCK2 mutation that initially had confounded results obtained using the strain. OT-II TCR transgenic mice X Thy 1.1 mice were a gift of Dr. L. Cohn (Yale University). All mice were bred in-house at the University of Pittsburgh. Wild type C57BL/6J controls were purchased from The Jackson Laboratory. All animals were housed under germ-free conditions and were used for experiments between 8 and 10 weeks of age.

Models of severe and mild/moderate asthma. These models have been described and evaluated in detail by us previously. Briefly, the severe asthma model consists of a sensitization phase where 25 μg of house dust mite antigen (HDM; Greer Laboratories and the lot selected for low endotoxin) is administered intratracheally to lightly anesthetized mice on d 1, 3, and 5 along with 5 μg of the bacterial product c-di-GMP (Biolog Inc.). Following a rest period of 5 d, the challenge phase consists of 3 sets of identical treatments each separated by 4 d of rest as follows: Day 1, 25 μg HDM+0.5 μg c-di-GMP; D 2 & 3, 25 μg HDM alone. Experiments aimed at analysis of the sensitization phase were performed on day 6 and those examining the full model on day 28. The mild/moderate asthma model was identical to the above except that no c-di-GMP was used. For experiments involving in vitro culture of APCs with OT-II TCR transgenic CD4$^+$ T cells, 100 μg of ovalbumin (OVA, low endotoxin; Sigma) was used in place of HDM.

Pulmonary function testing for assessing airway hyperresponsiveness. We have described assessment of AHR in mice in detail previously. Briefly, mice were anesthetized and subjected to the forced oscillation technique for measuring AHR using a Flexivent PFT apparatus (SCIREQ). Measurements of lung function were made following perturbation with increasing doses of methacholine.

Differential BAL cell counting and lung histology. Bronchoalveolar lavage was performed on anesthetized mice by infusion and recovery of 1 ml sterile PBS. Approximately 1×10$^5$ BAL fluid cells were placed onto glass slides by cytospin. Following air-drying, these slides were stained with Giemsa and macrophages, lymphocytes, eosinophils, and neutrophils were enumerated out a total of approximately 300 total cells.

For histology, lungs fixed in Safefix II (Fisher Scientific) were embedded in paraffin, sectioned, and stained with periodic acid-Schiff (PAS) reagent. An inflammation score on a scale of 0-4 was assigned to the perivascular and peribrochial areas of multiple fields per slide in blinded fashion. Approximately 8 mice per condition were scored. BAL cell differentials and lung histology slides were all read, and photomicroscopy performed, using a Zeiss Axiphot microscope mounted with a Zeiss AxioCam HRc camera.

Flow cytometry. Optimally diluted, directly labeled antibodies were used to stain surface markers in single cell suspensions in a volume of 100 μl FACS buffer (PBS+2% FCS) for 20 min at 0° C. For intracellular IFN-γ staining, in vitro-stimulated cells were treated with PMA (50 ng/ml) and ionomycin (500 ng/ml) for 5 h with brefeldin A (GolgiPlug; BD Biosciences) added during the final 3 h. The cells were fixed in 4% paraformaldehyde for 20 min at RT, followed by permeabilization (CytoPerm; BD Biosciences) for 30 min at 0° C., then optimally diluted antibody also for 30 min at 0° C. For these experiments, antibodies to the following molecules were used: CD4-PerCP Cy5.5 (L3T4), IFN-γ-APC (XMG1.2), CD11c-APC (HL3), CD11b-PE (M1/70), CD103-PE (M290), SiglecF-PE CF594 (E50-2440), CD45R/B220-PE (RA3-6B2) all from BD Biosciences, and MHC Class II-FITC (NIMR-4) from Southern Biotec. In all cases, appropriate isotype control antibodies were used in parallel. Data acquisition was performed on a FACSAria flow cytometer (BD Immunocytometry Systems). Final analysis was performed using FlowJo software (TreeStar).

Cell isolation and culture. Our cell isolation methods have been described in detail previously. Briefly, lung APCs (DCs and macrophages) were prepared from collagenase/DNAse-digested tissue using CD11c magnetic bead separation (Miltenyi Biotec). These two cell populations were then purified by cell sorting using a FACSAria cell sorter (BD Immunocytometry Systems) based upon autofluorescence and MHC Class II staining: lung macrophages are autofluorescence$^{high}$/MHC ClassII$^{low}$, and DCs are autofluorescence$^{low}$/MHC Class II$^{high}$. Lymph node migratory DCs (migDCs) were also sorted from single cell suspensions based upon the phenotype CD11c$^+$/MHC Class II$^{high}$/CD11b$^+$. Naïve CD4 TCR transgenic T cells were isolated from spleens of OT-II mice using a T cell isolation kit (Miltenyi Biotec), followed by cell sorting for the phenotype CD4$^+$/CD62L$^+$/CD44$^-$. CD62L-PE (MEL-14) and CD44-FITC (IM7) antibodies were both from BD Biosciences.

For in vitro restimulation, total lymph node cells were plated at 1×10$^6$ cells/ml in complete cell culture medium: RPMI 1640 (Gibco) supplemented with 10% heat-inactivated FBS (Gemini), 100 U/ml of penicillin and 100 μg/ml of streptomycin sulfate (Gibco), 1 mM sodium pyruvate (Gibco) and 50 μM 2-mercaptoethanol (Sigma). Depending upon the in vivo model being used, appropriate antigen, HDM (100 μg/ml) or OVA (100 μg/ml) was added. In certain experiments, 10 μg/ml no azide/low endotoxin anti-IL-10 neutralizing antibody (JES5-16E3) or appropriate control antibody (A95-1), both from BD Biosciences, was added for the duration of the culture incubation. Cultures were incubated for 72 h then IFN-γ or IL-12p40 expression was assessed by intracellular staining and ELISA.

Naïve OT-II CD4 cells (5×10$^5$ cells/well) were cultured with purified CD11c$^+$/MHC Class II$^{high}$ lymph node migDCs (0-2×10$^4$ DCs/well) isolated from sensitized mice and OVA (100 μg/ml). To assess in vitro priming, culture supernatants were tested for secreted IFN-γ by ELISA assay after 72 h of culture. In additional experiments to mimic T cell reactivation in the periphery, naïve OT-II were cultured as above with lymph node migDCs (2×10$^4$ DCs/well) for 7 d. At that time, the CD4$^+$ T cells were re-cultured with lung parenchymal DCs or macrophages isolated from sensitized animals and OVA, then IFN-γ was similarly assessed after 72 h.

Cytokine Measurements. Lung protein extracts were prepared by homogenizing tissue in 50 mM Tris-HCl, pH7.4, 150 mM NaCl, 0.02% Tween 20, and Complete Mini, EDTA-Free Protease Inhibitor (Roche Applied Science). These extracts were assessed for IFN-γ and IL-5 production using a multiplex assay (Bio-Rad Laboratories). Results were read using an automated system (Luminex; Bio-Rad Laboratories). Cell culture supernatants were assessed for IFN-γ and IL-12p40 by an ELISA assay incorporating DuoSet reagents (R&D Systems).

RNA Isolation and quantitative RT-PCR. Lung tissue was homogenized in TRIzol solution (Life Technologies), and cells (total lymph node or migDCs) were lysed by resuspension in RLT buffer (QIAGEN). RNA was prepared from each using an RNeasy kit (QIAGEN). qRT-PCR was performed using expression primer and probe sets from Life Technologies as follows: mouse IFNG (Mm01168134_m1), IL-5 (Mm004396646_m1), IL-12p35 (Mm00434165_m1), IL-12p40 (Mm00434174_m1), hprt1 (Mm01545300_m1), and human IRF5 (Hs00158114_m1), hprt1 (Hs02800695_m1). The reactions were performed at the University of Pittsburgh Genomics Research Core using the ABI PRISM 7700 Sequence System (Applied Biosystems). As an internal reference control, hprt1 was used to calculate mRNA expression using the $2^{-\Delta Ct}$ method.

Statistics. For paired analysis, the Mann-Whitney U test was used for nonparametric data, otherwise the Student's t test was performed. For multiple comparisons, such as BAL differential counts, one way analysis of variance (ANOVA) with Bonferroni's multiple comparison test, or the Kuskal-Wallis test with Dunn's multiple comparisons was performed. In each case, statistical significance was considered at p<0.05. *P≤0.05; P≤0.01; *P≤0.001; ****P≤0.0001. All statistical analyses were performed using GraphPad Prism Version 5 for OS X software.

Results

Increased BALF cell IRF5 expression in human severe asthma. IRF5 emerged as a candidate gene for association with SA given its capacity to induce CD4$^+$ T cell IFN-γ secretion via expression of cytokines such as IL-12 in antigen presenting cells in vitro. High expression of IFN-γ is now recognized as a cardinal feature of a particular subset of SA in humans, which we have recapitulated in our recently developed murine model. Based on these findings, we examined IRF5 expression in human BAL cells, which include not only lymphocytes, but also a very high percentage of macrophages. As shown in FIG. 2, panel A, we observed a significantly higher IRF5 expression in human BALF cells collected from severe asthmatics as compared to that in cells from mild asthmatics or healthy controls.

IRF5 deficiency impairs airway hyperresponsiveness in murine severe asthma. We next utilized IRF5$^{-/-}$ mice to determine the importance of IRF5 in promoting AHR and the high Th1 profile in the model of SA. The model consists of allergen sensitization with house dust mite (HDM), combined with the bacterial product cyclic-di-GMP (c-di- GMP) in order to induce a strong Th1 response, followed by additional challenges with HDM over a 28 d period. The general approach used was to compare the IRF5$^{-/-}$ mice with WT animals at different levels including airway inflammation, immune priming in the lymph nodes, reactivation in the periphery, and physiologic outcome.

Initially, IRF5$^{-/-}$ mice were subjected to the experimental model of SA and were assessed for inflammatory cell infiltration of the airways. Histology of lung sections revealed that the overall level of inflammation was comparable between WT and IRF5$^{-/-}$ animals (FIG. 2, panel B). Semi-quantitative, blinded scoring showed no difference in overall inflammation in either peribronchial or perivascular areas (FIG. 2(B)). Importantly however, AHR (airway resistance, Rn) in response to methacholine challenge was significantly diminished in IRF5$^{-/-}$ mice as compared to that induced in WT animals (FIG. 2, panel C) in a manner similar to what we had previously reported using IFN-γ$^{-/-}$ mice. This effect was not observed in a model of mild/moderate (M/MOD) asthma where IFN-γ expression is not a prominent feature (essentially, HDM without the c-di-GMP adjuvant) (FIG. 2, panel D). If anything, AHR trended higher for the IRF5$^{-/-}$ mice in the mild/moderate model although the difference did not reach significance. These results suggested that a deficit in IFN-γ production in IRF5$^{-/-}$ mice might be responsible for decreased AHR, given that this effect was seen in the IFN-γ high SA, but not in the IFN-γ low M/MOD, model. BALF cell cytospins and differential cell counts revealed a significantly elevated percentage and number of eosinophils in IRF5$^{-/-}$ mice compared to that in WT mice (FIG. 2, panel E). This is in spite of total BALF cell numbers being similar (6.37±2.06 versus 5.43±2.59 million total BAL cells/mouse for WT and IRF5$^{-/-}$ mice, 8 mice/group, respectively). In contrast to an increase in percentage of eosinophils, a significant decrease in the percentage of neutrophils was observed in IRF5$^{-/-}$ mice although the decrease in the number of neutrophils did not reach statistical significance (FIG. 2, panel E). Neutrophilia has been associated with IL-17 production including in HDM-based murine models of asthma. So decrease in neutrophils suggests a reduction in Th17-type cytokines, which has been also reported with IRF5 deficiency and that we have also observed. However, in this study, we have focused on the Th1-type response due to the critical role of IFN-γ and not IL-17 in AHR in the context of a SA phenotype.

Lymph node dendritic cells have reduced capacity to promote IFN-γ production in the absence of IRF5. We next sought to determine if in fact a cytokine shift away from a type I response was occurring, specifically if IFN-γ was reduced in IRF5$^{-/-}$ mice during SA, and whether it was evident at the level of immune priming in the lymph nodes and/or during the effector phase in the lung. Although the function of IRF5 in dendritic cells (DCs) has not been described heretofore in any detail, we chose to closely examine these cells since they are centrally involved in immune priming in the lung-draining lymph nodes and qualitatively direct T helper cell differentiation via cytokines such as IL-12 and among others as previously published.

Figure 3:
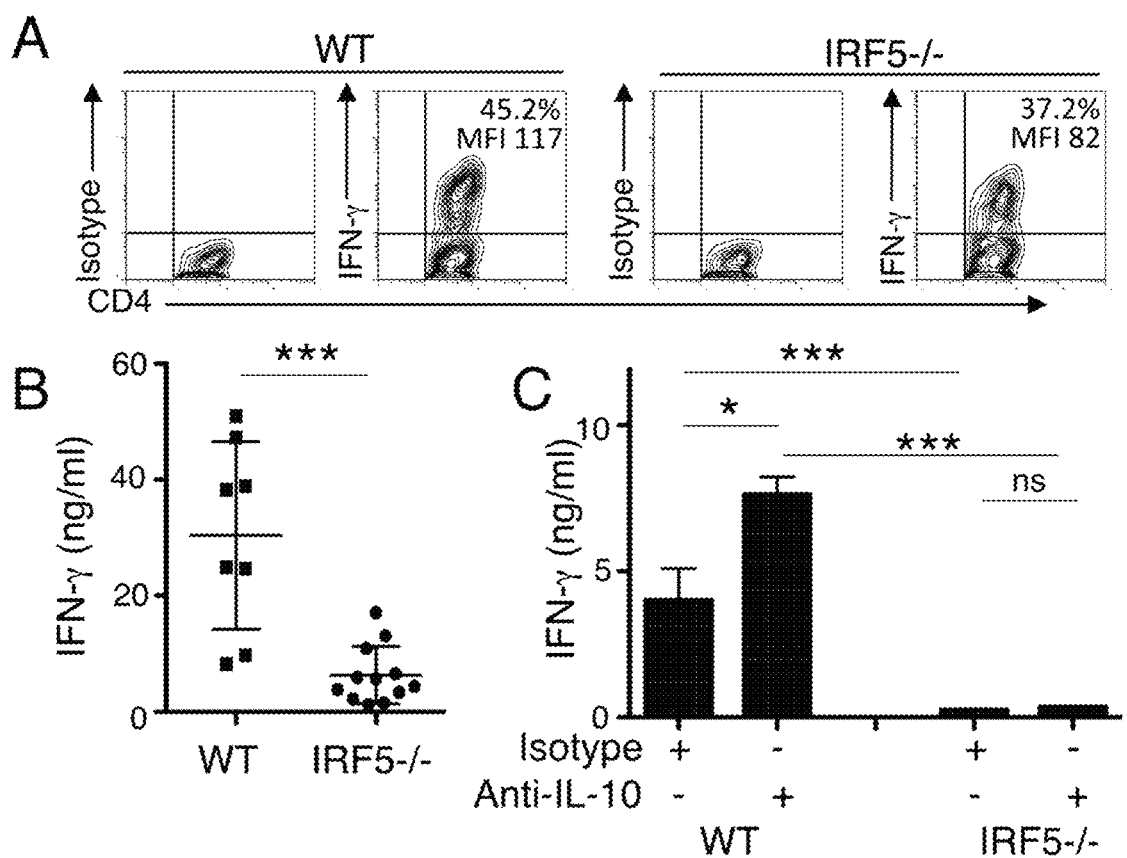
FIG. 3 shows IFN-γ in lymph nodes during the sensitization phase of murine severe asthma in IRF5$^{-/-}$ mice. Lymph nodes were harvested one day following sensitization with HDM+c-di-GMP on d 1, 3, and 5. Panel A shows total lymph node cells were re-stimulated in vitro for 72 h with HDM, then intracellular cytokine staining was performed to assess IFN-γ production from CD4$^+$ T cells. Panel B shows soluble IFN-γ production from re-stimulated in vitro lymph node cultures assessed by ELISA (n=8 WT, 12 IRF5$^{-/-}$ mice). Panel C shows IFN-γ production by total lymph node cells obtained from sensitized mice cultured with HDM and either neutralizing antibody to IL-10 or appropriate isotype control antibody (cells pooled from 4-5 mice per group then cultured in triplicate wells). *$P \leq 0.05$, ***$P \leq 0.001$ for unpaired Student's unpaired t test (panel B) or Kruskal-Wallis with Dunn's multiple comparison test (panel C). Data are mean±SEM and are representative of 3 independent experiments.

After priming WT and IRF5$^{-/-}$ mice with HDM+c-di-GMP (treatments on d 1, 3, and 5), the lung draining lymph nodes were harvested 24 h later, pooled (4-5 mice) and restimulated with HDM for 72 h in vitro. At the end of the culture period, intracellular cytokine staining revealed a modest decrease in the percentage of CD4$^+$ T cells capable of producing IFN-γ from IRF5$^{-/-}$ mice (45.2% versus 37.2% of total CD4 for WT and IRF5$^{-/-}$, respectively) (FIG. 3, panel A). However, the mean fluorescence intensity (MFI) of the IFN-γ$^+$ cells from IRF5$^{-/-}$ animals was also lower suggesting lower cytokine/cell that would result in reduced levels of secreted cytokine. Indeed, there was a significant reduction in secreted IFN-γ in cultures of cells from IRF5$^{-/-}$ compared to WT mice (FIG. 3, panel B). Secretion of IL-17 was also significantly reduced in cultures containing IRF5-deficient cells relative to WT (see, Oriss et al. IRF5 distinguishes severe asthma in humans and drives Th1 phenotype and airway hyperreactivity in mice. *JCI Insight* 2017 2:e9019), which might help explain the decreased neutrophilia discussed above. Given that neutrophils have been associated with additional features of severe asthma pathogenesis, examination of this aspect is crucial to collective understanding of immune mechanisms, and will be addressed in future investigations.

A consideration to go along with its effect of enhancing expression of Th1- and Th17-promoting cytokines, is that IRF5 has also been reported to suppress expression of the immune-modulating cytokine IL-10 thus prompting assessment of the effect of blocking its function. Compared to treatment of pooled lymph node cultures in vitro with the appropriate isotype control antibody, neutralizing anti-IL-10 effectively and significantly increased IFN-γ production from WT total lymph node cells indicating that its immunosuppressive effect was at least partially mitigated (FIG. 3, panel C). Importantly however, IL-10 neutralization failed to enhance IFN-γ production from IRF5$^{-/-}$ cultures. This suggests that any effects on IFN-γ-promoting cytokines predominate over any role that IL-10 may have at least at the level of T helper cell reactivation. IL-10 might have a larger role during effector phase responses in the periphery compared to priming in the lymph nodes, but that is beyond the current focus on regulation of IFN-γ promotion by DCs.

Figure 4:
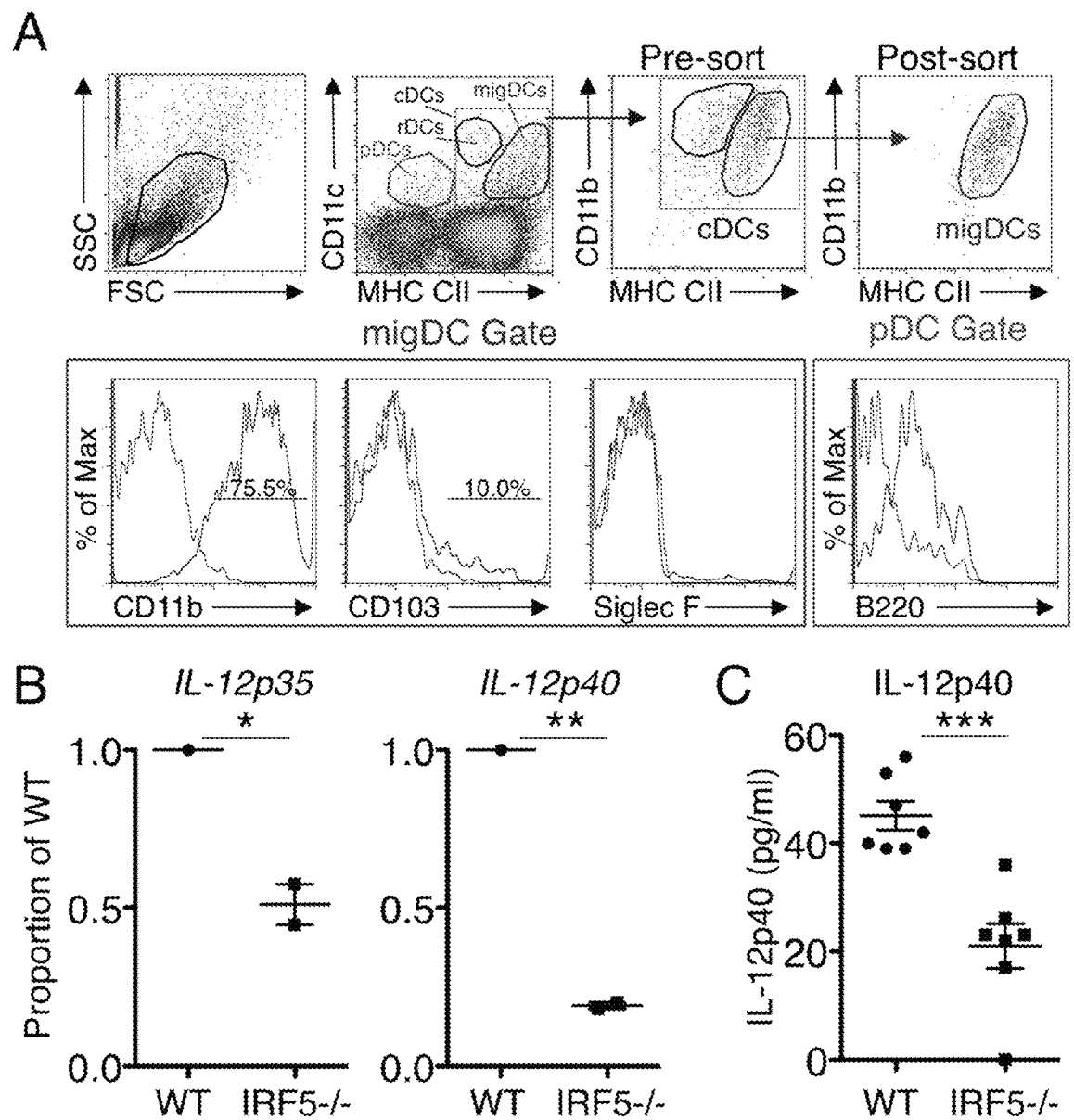
FIG. 4 shows lymph node migratory DCs from IRF5$^{-/-}$ mice are deficient in IL-12 and production during the sensitization phase of murine severe asthma. Mice were sensitized as in FIG. 2. Panel A shows migratory DCs with the phenotype CD11c$^+$/MHC Class II$^{high}$ were purified by fluorescence activated cell sorting. Panel B shows qRT-PCR was performed on purified migratory DCs for IL-12p35, IL-12p40. Data are the mean±SEM proportion of expression in IRF5$^{-/-}$ relative to WT for two independent, combined experiments. Panel C shows total lymph node cells were cultured as in FIG. 2 and soluble IL-12p40 was assessed by ELISA. Data are mean±SEM of 7 mice per group and representative of 2 independent experiments. *P≤0.05, P≤0.01, *P≤0.001 unpaired Student's unpaired t test.

Next we assessed IL-12 gene expression in CD11c$^+$ lymph node migratory dendritic cells since it is the primary cytokine associated with generation of T cells that produce IFN-γ. Plasmacytoid DCs (pDCs) in the lung can be distinguished from conventional DCs (cDCs) based upon relatively low level of expression of MHC Class II combined with B220 expression. A small population of pDCs was also detected in these lymph nodes. Among cDCs, it is well-established that lymph node resident DCs (rDCs) and migratory DCs (migDCs) are distinguished from each other based upon expression of CD11c, and high MHC Class II in the latter compared to more intermediate expression in the former. During the priming phase of the SA model, lung draining lymph node migDCs were largely positive for CD11b with only a very minor population of CD103$^+$ cells (75.5% and 10.0% of the cDC population, respectively), and no detectable macrophages based upon Siglec F staining (FIG. 4(A)). We have found that plotting MHC Class II versus CD11b in CD11c$^+$ cDC-gated cells also facilitates separation of migDCs from lymph node rDCs with intermediate expression of MHC Class II (FIG. 4, panel A). It is important to note that the DC phenotype profile shown in FIG. 4, panel A is representative of both WT and IRF5-deficient lymph node cells which were essentially identical. Utilizing these criteria, we purified migDCs, by fluorescence activated cell sorting. RNA was isolated from the sorted cells and qRT-PCR was performed for a number of cytokines. This analysis revealed significantly decreased levels of IL-12p35 and IL-12p40 RNA in migDCs from IRF5$^{-/-}$ mice compared to those in cells from WT mice (FIG. 4, panel B). Additionally, IRF5 has been reported to enhance expression of IL-6 and IL-23p19 in macrophages. While IL-6 mRNA level was also reduced in IRF5-deficient migDCs, IL-23p19 mRNA was not detected in lymph node DCs from either WT or IRF5$^{-/-}$ mice (data not shown). The number of migDCs that could be obtained via cell sorting was not conducive to measuring IL-12 protein from purified cells, however in total lymph node cultures, a significant decrease in IL-12p40 protein was noted in IRF5$^{-/-}$ mice (FIG. 4, panel C). IL-12p70, which is composed of the two subunits IL-12p35 and IL-12p40, was below the level of detection in these cultures. Although the p35 subunit of IL-12 is constitutively expressed in most cell types, the expression of the p40 subunit is inducible in hematopoietic cells such as DCs. However, the p40 subunit of IL-12 is produced in excess relative to the p35 subunit, with the latter determining the level of secreted IL-12 p70. Given that the p40 levels were low at the priming stage, the level of secreted IL-12 p70 was below the level of detection in the lymph node cultures.

Figure 5:
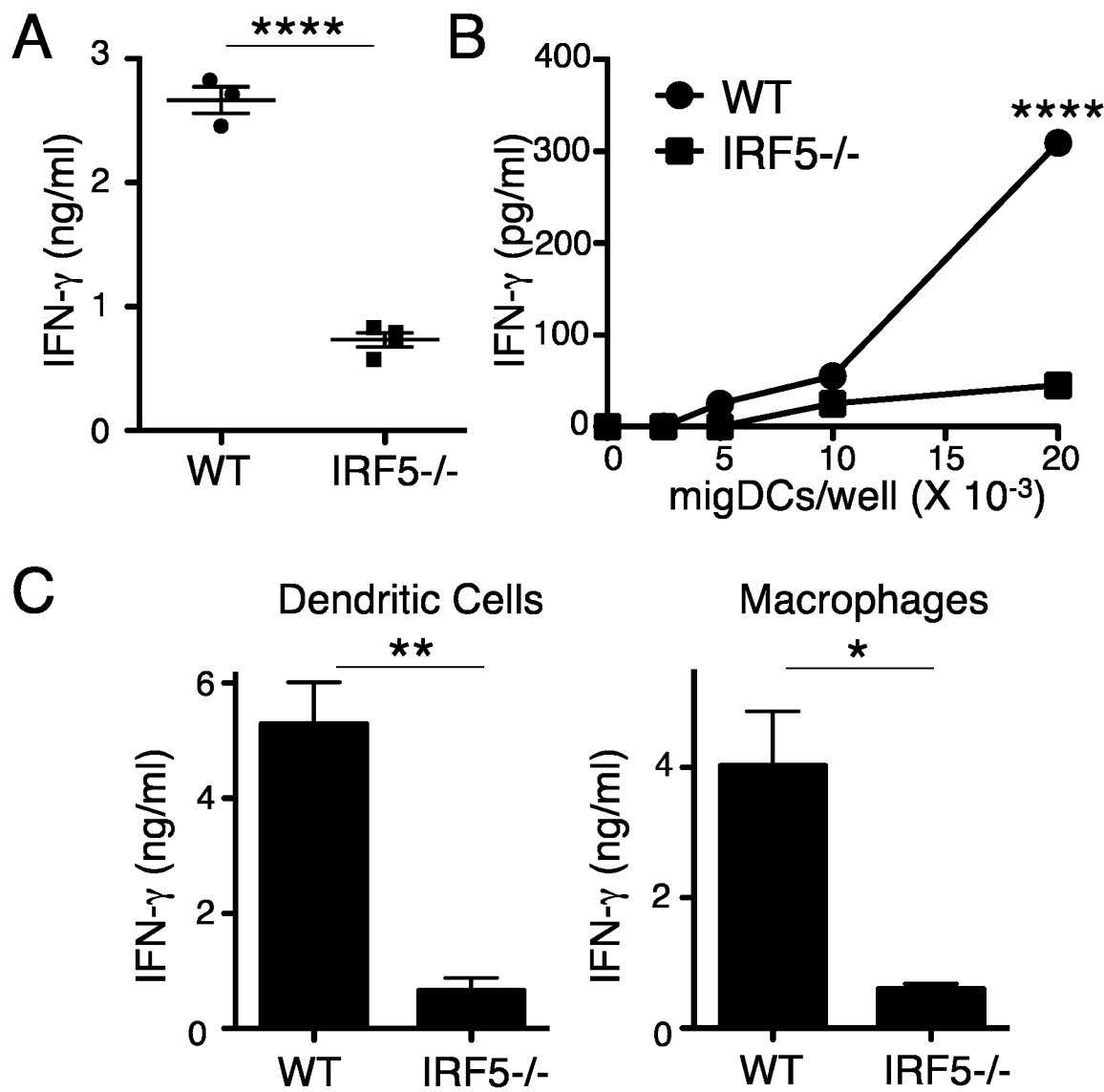
FIG. 5 shows that IRF5$^{-/-}$ DCs, deficient in IL-12 production, have reduced capacity to promote T cell IFN-γ production. Lymph nodes were harvested one day following sensitization with OVA+c-di-GMP on d 1, 3, and 5. Panel A shows total lymph node cells were re-stimulated in vitro for 72 h with OVA and soluble IFN-γ production was assessed by ELISA (n=3 WT, 4 IRF5$^{-/-}$ mice). Panel B shows increasing numbers of lymph node DCs purified by cell sorting as in FIG. 3 were co-cultured with OVA and naïve (CD62L$^{high}$/CD44$^{low}$) spleen OT-II TCR transgenic CD4$^+$ T cells similarly purified by cell sorting. Soluble IFN-γ production was assessed at 72 h of culture. Panel C shows lymph node DCs and naïve OT-II CD4$^+$ T cells were cultured as in B for 7 d. The expanded T cells were subjected to a second round of stimulation with specific peptide and either lung DCs or macrophages purified from sensitized mice by cell sorting. After 72 h of secondary in vitro culture, soluble IFN-γ was measured. Data are mean±SEM of triplicate cultures of pooled cells from 3-5 mice per group. *P≤0.05, ***P≤0.001 for unpaired Student's unpaired t test. Each experiment was performed 2 independent times.

Given the difference between WT and IRF5$^{-/-}$ lymph node migDCs in terms of IL-12 expression, their function in promoting T cell priming and differentiation was examined. This series of experiments was performed using the OVA system due to having access to specific TCR transgenic mice (OT-II, specific for OVA). Mice were treated in a manner identical to priming in the SA model with c-di-GMP, but with OVA substituted for HDM. Use of OVA as an antigen also resulted in decreased IFN-γ in total lymph node cell cultures (FIG. 5, panel A) additionally demonstrating that IRF5-mediated effects are not antigen-specific. Migratory lymph node DCs were then purified as described above, then co-cultured in vitro with OVA, and naïve (CD62L$^{high}$/CD44$^{low}$) OT-II TCR transgenic spleen T cells, which were also purified by cell sorting. Assessment of soluble cytokines in culture supernatants at 72 h of incubation also revealed significantly lower IFN-γ levels in cultures containing IRF5$^{-/-}$ DCs compared to WT DCs (FIG. 5, panel B). These data suggested that decreased IL-12 production in the latter is directly related to deficiency in IFN-γ-promoting capacity during priming in the lymph nodes.

Once priming occurs, T cells exit the lymph nodes and return to the periphery to await potential reactivation. Therefore, we assessed IFN-γ production from T cells that had been primed in vitro with lymph node DCs as described above after restimulation. In order to mimic the in vivo situation as closely as possible, in vitro-primed CD4$^+$ T cells were re-stimulated after 7 d with lung-derived DCs, but also with macrophages which can similarly serve as APCs in the periphery. Lung tissue DCs and macrophages were purified from HDM+c-di-GMP-treated mice by CD11c$^+$ magnetic separation followed by cell sorting based upon autofluorescence, CD11c/MHC Class II co-expression as previously described. After an additional 72 h of culture of the primed T cells, it was clear that APCs from IRF5$^{-/-}$ mice supported significantly lower level of soluble IFN-γ production compared to those from WT mice regardless of whether lung DCs or macrophages were used as APCs (FIG. 5). These data show that the initial deficit in IFN-γ production in the lymph nodes of IRF-5$^{-/-}$ mice is amplified in the periphery (FIG. 2).

Figure 6:
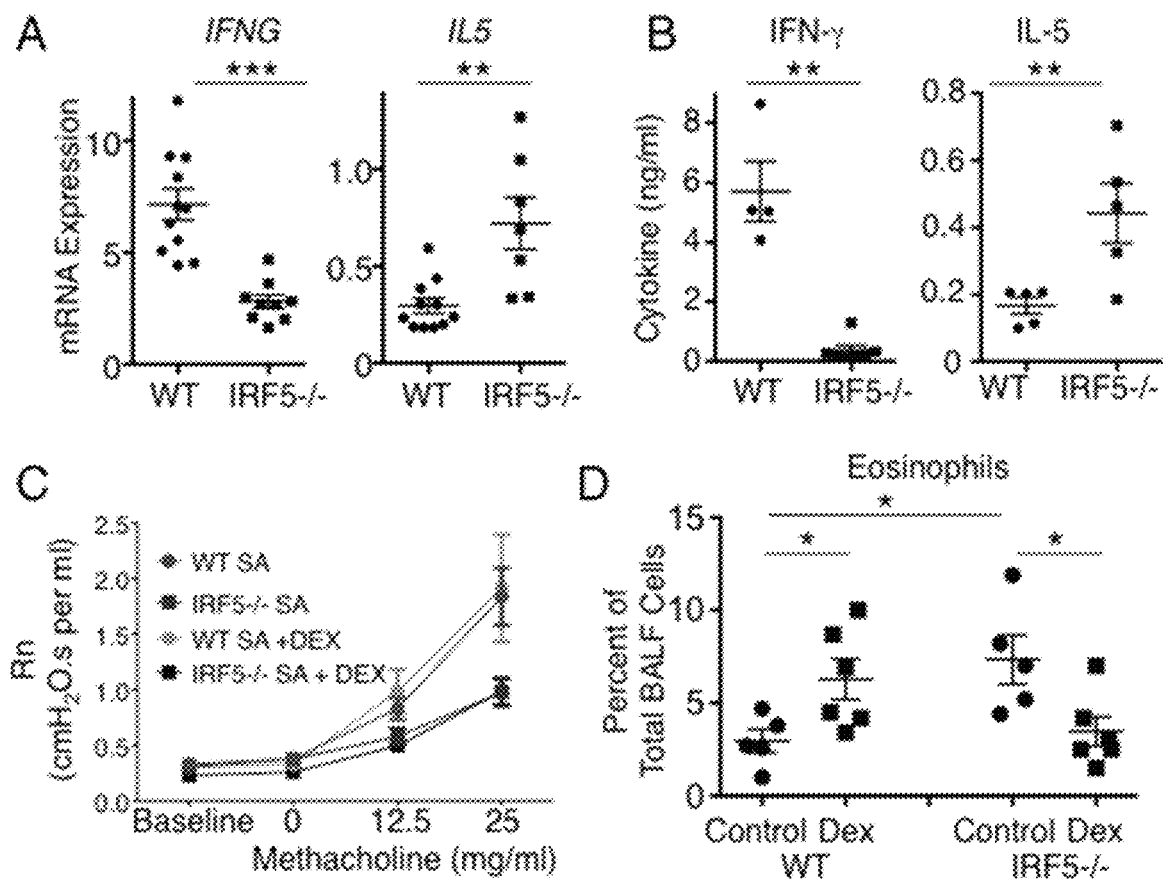
FIG. 6 shows inhibition of increased eosinophilia in IRF-5$^{-/-}$ mice with CS treatment. Mice were subjected to the full 28-day model of severe asthma encompassing sensitization followed by repeated challenge. Panel A shows whole lung qRT-PCR for IFN-γ and IL-5 mRNA levels. Panel B shows IFN-γ and IL-5 protein levels in lung tissue homogenate (A-B; n=4-7 mice per group). Panel C shows airway hyperresponsiveness (Rn) in WT and IRF5$^{-/-}$ mice with or without steroid (dexamethasone, Dex) treatment. Panel D shows BAL eosinophilia in WT and IRF5$^{-/-}$ mice with or without steroid (dexamethasone, Dex) treatment (panels C-D; n=5-8 mice per group). Data are mean±SEM and each experiment was performed at least 2 independent times. *P≤0.05, P≤0.01, *P≤0.001 for unpaired Student's unpaired t test (panels A-B), one way ANOVA with Bonferroni's multiple comparison test (panel C), or Kuskal-Wallis Test with Dunn's multiple comparison test (panel D).

Significantly decreased IFN-γ in lung tissue in IRF5$^{-/-}$ mice. In order to determine if the IRF5$^{-/-}$ mice display a deficit in IFN-γ in the lungs during severe asthma, the full 28 day model was run and total lung extracts were prepared for RNA and protein estimation. qRT-PCR revealed the expected reduction of IFN-γ in IRF5$^{-/-}$ mice relative to that in the WT counterparts (FIG. 6, panel A). Interestingly, IL-5 mRNA was reciprocally increased in IRF5$^{-/-}$ mice relative to WT animals in this model (FIG. 6, panel A). This is most likely due to immune cross-regulation since no direct transcriptional effects of IRF5 on Th2-cytokines has been described. At the protein level, secreted IFN-γ in the lung tissue was also significantly reduced with concomitant increase in IL-5 (FIG. 6, panel C). Thus, this cytokine expression profile in IRF5$^{-/-}$ and WT mice explained the concomitant lower AHR (FIG. 2, panel C) and higher eosinophilia (FIG. 2) that is observed in the former.

Alleviation of increased eosinophilia in IRF-5$^{-/-}$ mice with CS treatment. The data presented in the previous section shows that inhibition of one arm of the immune response in vivo induced reciprocal effects that could be deleterious. Thus, while IRF5 deficiency caused inhibition of Th1 response and AHR, it resulted in increase in Th2 response and eosinophilia, which is known to adversely impact airway disease. As expected based upon our previous data obtained with BALB/c mice, the development of AHR in C57 mice was completely resistant to treatment with the CS dexamethasone in both WT and IRF5$^{-/-}$ mice (FIG. 6, panel C). However, treatment with dexamethasone blunted the increase in airway eosinophilia, CS being known to promote the apoptosis of eosinophils (FIG. 6, panel D). Furthermore, this effect was observed both in WT animals and the IRF5$^{-/-}$ mice, which exhibited significantly higher eosinophilia in the SA model in the absence of CS treatment (FIG. 6, panel D). All of the aforementioned data have now been published (Oriss et al. IRF5 distinguishes severe asthma in humans and drives Th1 phenotype and airway hyperreactivity in mice. *JCI Insight* 2017 2:e9019) along with additional information demonstrating compensatory Th2 response in IRF5$^{-/-}$ mice highlighted by increased IL-4, IL-13, and antigen-specific IgG1, all of which become responsive to steroid treatment in the setting of IRF5 deficiency. These data suggest that specific immune processes might be amenable to targeted therapeutic strategies in SA, where treatment options currently are limited.

Example 2—Using IRF5 Antisense Oligonucleotides (ASOs)

As shown in Example 1, BAL cells in SA subjects express a higher level of the transcription factor IRF5 compared to cells from mild asthmatics (MA) or healthy controls (HCs). IRF5-deficient dendritic cells (DCs) in lung-draining lymph nodes have blunted IL-12 (Th1-inducing) and elicit poor Th1 priming when IRF5$^{-/-}$ mice are subjected to the SA model. When the IRF5$^{-/-}$ mice are subjected to the SA model, they show a significantly lower IFN-γ levels in the lungs and also display attenuated airway hyperresponsiveness (AHR). Of note, the increase in type 2 immune response observed in the IRF5$^{-/-}$ mice can be alleviated using CS. Additional data further demonstrating these effects on type 2 cytokines as well as on downstream effects including the level of antigen-specific IgG1 levels are found in Oriss et al. IRF5 distinguishes severe asthma in humans and drives Th1 phenotype and airway hyperreactivity in mice. *JCI Insight* 2017 2:e9019. This shows that simply deleting IRF5 renders the mice responsive to CS and thus a combination of anti-IRF5 agent plus low dose CS has the potential to squelch all arms of the immune response in SA. Interestingly, IRF5 expression in lung DCs and macrophages is also required to maintain high level IFN-γ production from primed Th1 cells, which our data suggest is due to IRF5-mediated suppression of IL-10 production. As such, inhibition of IRF5 is expected to alleviate disease symptoms in steroid-refractory SA.

Materials and Methods

Mouse Strains

Wild-type (WT) C57BL/6 WT and IRF5$^{-/-}$ mice on C57BL/6J background, and confirmed to be free of the DOCK2 mutation.

Mouse Model of Severe Asthma and Effect of IRF5 ASOs

25 µg of house dust mite antigen (HDM; Greer Laboratories and the lot selected for low endotoxin) is administered intratracheally to lightly anesthetized mice on days 1, 3, and 5 along with 5 µg of the bacterial product c-di-GMP (Biolog Inc.). Following a rest period of 5 d, the challenge phase consists of 3 sets of identical treatments each separated by 4 days of rest as follows: day 1-25 µg HDM+0.5 µg c-di-GMP; days 2 & 3, HDM alone. After the last HDM challenge, the mice are analyzed on day 28. WT C57BL/6 and BALB/c mice will be sensitized as above. After the rest period of 5 days, non-specific oligonucleotide or IRF5 mouse-specific ASO is delivered using an oropharyngeal and intranasal mode before initiating challenge with HDM+c-di-GMP. Dose and frequency of delivery is to be based on experience in other airway models and stability of ASOs in vivo. A nose-only aerosol delivery method may be examined. An additional control in these experiments is IRF5$^{-/-}$ mice, which have no expression of IRF5 mRNA in any cell type.

Pulmonary function testing for assessing airway hyperresponsiveness (AHR). Briefly, mice are anesthetized and subjected to the forced oscillation technique for measuring AHR using a FlexiVent PFT apparatus (SCIREQ). Measurements of lung function are made following perturbation with increasing doses of methacholine.

Differential BAL cell counting and lung histology. BAL is performed on anesthetized mice by infusion and recovery of 1 ml sterile PBS. Approximately $1 \times 10^5$ BAL fluid cells are placed onto glass slides by cytospin. Following air-drying these slides are stained with Giemsa and macrophages, lymphocytes, eosinophils, and neutrophils are enumerated out of a total of approximately 300 total cells.

For histology, lungs fixed in Safefix II (Fisher Scientific) are embedded in paraffin, sectioned, and stained with periodic acid-Schiff (PAS) reagent. An inflammation score on a scale of 0-4 is assigned to the perivascular and peribrochial areas of multiple fields per slide in a blinded fashion. Approximately 4-8 mice per condition are scored. BAL cell differentials and lung histology slides are all read, and photomicroscopy performed, using a Zeiss Axiphot microscope mounted with a Zeiss AxioCam HRc camera.

RNA Isolation and quantitative RT-PCR. Lung tissue is homogenized in TRIzol solution (Life Technologies). Cells (total lymph node or migDCs) are lysed by suspension in RLT buffer (QIAGEN). RNA is prepared from each using an RNeasy kit (QIAGEN). qRT-PCR is performed using expression primer and probe sets from Life Technologies. Expression relative to hprt mRNA expression is assessed.

Flow cytometry. Optimally diluted, directly labeled antibodies are used to stain surface markers in single cell suspensions. For intracellular cytokine staining, cells are treated with PMA (50 ng/ml) and ionomycin (500 ng/ml) for 5 h with brefeldin A (GolgiPlug; BD Biosciences) added during the final 3 h. The cells are fixed in 4% paraformaldehyde for 20 min at RT, followed by permeabilization (CytoPerm; BD Biosciences) for 30 min at 0° C., then optimally diluted antibody is added for 30 min at 0° C. In all cases, appropriate isotype control antibodies are used in parallel. Data acquisition is performed on a FACSAria flow cytometer (BD Immunocytometry Systems). Final analysis is performed using FlowJo software (TreeStar).

Cell isolation and culture. Lung or lymph-node antigen-presenting cells (APCs-DCs and macrophages) are prepared from collagenase/DNase-digested tissue using CD11c magnetic bead separation (Miltenyi Biotec). These two cell populations are then purified by cell sorting using a FACSAria cell sorter (BD Immunocytometry Systems) based on cell surface expression of cell-specific molecules. Naïve CD4 TCR transgenic T cells are isolated from spleens of OT-II mice using a T cell isolation kit (Miltenyi Biotec), followed by cell sorting for the phenotype CD4$^+$/CD62L$^+$/CD44$^-$. Cultures are incubated for 72 h after which cytokine production is assessed by intracellular staining and/or ELISA.

Statistical analysis. To compare data obtained from two or more groups of mice, we will use the Kruskal-Wallis Rank Sum test followed by multiple comparisons using Dunn's test. Where appropriate, comparison between more than two groups of mice will be made using a one way analysis of variance (ANOVA) with subsequent multiple comparisons made using Tukey test. For all tests, differences will be considered statistically significant when $p \leq 0.05$.

Expected Results. Collectively, based on our established experimental mouse model and tissue culture systems that show a role for IRF5 expression in lung DCs for both priming and reactivation of Th1 cells, we expect that targeting IRF5 using a specific agent such as IRF5 ASO will attenuate the Th1 response as well as AHR in the animals subjected to the SA model. The studies in mice as well as using human samples will require some initial dose and delivery optimization.

Cell Culture Studies Using IRF5 ASOs

Effect of IRF5 ASO during priming and T cell reactivation using mouse system. For effect on priming, assays using naïve T cells from OT-II TCR transgenic mice and LN DCs from WT C57BL/6 mice sensitized with HDM+c-di-GMP±control oligo or IRF5 ASOs at different doses are used. To examine effect on reactivation, after primary culture over 7 days, T cells are recovered and restimulated with lung DCs isolated from mouse lungs on day±6 after sensitization±control and IRF5 ASOs. Again, DCs from IRF5$^{-/-}$ mice are used as controls. IL-12, IFN-γ and IL-10 present in the culture supernatant will be assayed by ELISA. Depending on data, we will also assay IL-17 and type 2 cytokine (IL-5 and IL-13) levels in the supernatant.

Effect of IRF5 ASO using PBMCs from healthy controls (HC), mild asthma and severe asthma subjects. Peripheral blood mononuclear cells (PBMCs) are purified from whole blood by density gradient centrifugation (Ficoll-Hypaque). Cells will be placed in culture ($1 \times 10^6$ cells/1 ml/well) and stimulated with T cell activation beads (1 bead/2 cells; Miltenyi Biotec) or anti-CD3 antibody in the presence or absence of c-di-GMP±control and human-specific IRF5 ASOs. Cells are cultured for 5 days and culture supernatants are collected for cytokine (IL-12, IFN-γ, IL-10 and others) assay. SNP studies of the IRF5 gene in all of these samples because IRF5 expression is higher in BAL cells of SA subjects as compared to that in cells from HCs and subjects with milder disease. While BAL cells already show upregulation of IRF5 in the SA subjects, which could be due to local infection or other causes (SNPs), it may be necessary to use stimuli (LPS, c-di-GMP) to induce IRF5 in the peripheral blood monocytes. Alternatively, macrophages generated from the monocytes in vitro and co-culture with isolated T cells from the same PBMCs in the presence of activation beads can be used.

Expected Results. First, this assay system may prove useful as a high-throughput approach to determine whether blockade of IRF5 would dampen IL-12 and IFN-γ production from human PBMCs. HCs are expected not to have basal expression of IRF5 in myeloid cells. BAL cells in some mild/moderate asthma subjects express slightly higher levels while cells in SA subjects relatively express the highest level (of note-none of the BAL samples was stimulated ex vivo and reflect in vivo steady-state levels). However, peripheral blood monocytes may not show this difference between subjects since expression may be induced by local stimuli. What would be most interesting to determine is whether exposure to c-di-GMP would cause increase in IRF5 expression in peripheral blood cells from some SA subjects and whether it would be associated with SNPs in the IRF5 gene that cause higher level of IRF5 mRNA expression or stabilization of the IRF5 protein. Alternatively, higher level of IRF5 expression in cells of SA subjects may be induced by specific infectious agents that produce potent inducers such as c-di-GMP. Additional unknown gene-environment interactions may underlie the propensity for higher IRF5 expression in myeloid cells in severe asthmatics. The data generated in the above studies will also provide a wealth of information about the relevance of IRF5 in promoting a high type 1/IFN-γ response in SA.

Further embodiments or aspects are set forth in the following numbered clauses:

Clause 1: A method of treating asthma in a patient, comprising reducing IRF5 activity to a level effective to treat one or more symptoms of asthma in a patient.

Clause 2: The method of clause 1, wherein the asthma is corticosteroid-insensitive.

Clause 3: The method of clause 1 or clause 2, wherein the patient displays a Th1, optionally a Th1/Th17hiTh2lo, immune profile.

Clause 4: The method of any of clauses 1-3, comprising administering an effective amount of corticosteroid to the patient, either systemically or locally in the respiratory tract, along with reducing IRF5 activity in the patient.

Clause 5: The method of any of clauses 1-4 wherein IRF5 expression is reduced by administering to the patient a nucleic acid or an analog thereof able to decrease (e.g., silence or stop expression of) IRF5 in the patient.

Clause 6: The method of clause 5, wherein the nucleic acid or analog thereof is an antisense reagent.

Clause 7: The method of clause 5, wherein the nucleic acid or analog thereof is an interfering nucleic acid or analog thereof acting by RNA interference (RNAi).

Clause 8: The method of clause 7, wherein the interfering nucleic acid or analog thereof is an interfering microRNA (miRNA) reagent or an interfering small interfering RNA (siRNA) reagent.

Clause 9: The method of clause 5, wherein the nucleic acid or analog thereof is a ribozyme reagent.

Clause 10: The method of any of clauses 1-9, wherein IRF5 activity is decreased using a binding reagent specific to IRF5, such as an anti-IRF5 antibody, or antibody fragment, such as a recombinantly-produced scFv fragment (recombinant IRF5 antibodies are commercially-available and are broadly-known).

Clause 11: A composition, such as an inhaled dosage form, for treatment of asthma, such as corticosteroid-refractory, or severe asthma, comprising a corticosteroid and an interfering nucleic acid, such as a miRNA or an siRNA, or an interfering RNA able to down-regulate expression of IRF5 in a patient.

While the present invention is described with reference to several distinct embodiments, those skilled in the art may make modifications and alterations without departing from the scope and spirit. Accordingly, the above detailed description is intended to be illustrative rather than restrictive.

We claim:

1. A method of treating severe asthma in a patient, comprising administering to the patient a composition comprising:
   a corticosteroid; and
   a nucleic acid or an analog thereof able to decrease IRF5 expression in the patient in an amount effective to reduce IRF5 activity to a level effective to treat one or more symptoms of asthma in the patient.

2. The method of claim 1, wherein the patient displays a Th2$^{lo}$ immune profile.

3. The method of claim 1, wherein the patient has corticosteroid-insensitive asthma.

4. The method of claim 1, wherein the nucleic acid or analog thereof is an antisense reagent.

5. The method of claim 1, wherein the nucleic acid or analog thereof is an interfering nucleic acid.

6. The method of claim 5, wherein the interfering nucleic acid is an RNA.

7. The method of claim 6, wherein the RNA is a microRNA reagent or a small interfering RNA reagent.

8. The method of claim 1, wherein the composition is administered through delivery to the patient's respiratory tract.

9. The method of claim 8, wherein the composition is administered daily.

10. The method of claim 8, wherein the composition is administered with a metered dose inhaler.

11. The method of claim 8, wherein the composition is administered with a nebulizer.

12. The method of claim 1, wherein the nucleic acid or an analog thereof has the sequence of SEQ ID NO: 7 or a sequence complementary thereto or the sequence of SEQ ID NO: 8 or a sequence complementary thereto.

13. An aerosolizable or nebulizable composition comprising:

a pharmaceutically-acceptable carrier;
a corticosteroid; and
a nucleic acid or an analog thereof able to decrease IRF5 expression in a patient in an amount effective to reduce IRF5 activity to a level effective to treat one or more symptoms of asthma in the patient.

14. The composition of claim 13, wherein the composition has a particle size in a range of 20 μm to 500 μm and is configured to be administered by inhalation.

15. The composition of claim 13, wherein the nucleic acid or analog thereof is an antisense reagent.

16. The composition of claim 13, wherein the nucleic acid or an analog thereof is an interfering nucleic acid.

17. The composition of claim 16, wherein the interfering nucleic acid is an RNA.

18. The composition of claim 17, wherein the interfering nucleic acid is a microRNA reagent or a small interfering RNA reagent.

19. The composition of claim 13, wherein the nucleic acid or an analog thereof has the sequence of SEQ ID NO: 7 or a sequence complementary thereto, or the sequence of SEQ ID NO: 8 or a sequence complementary thereto.

\* \* \* \* \*

SEQUENCE LISTING

```
<160> NUMBER OF SEQ ID NOS: 10

<210> SEQ ID NO 1
<211> LENGTH: 498
<212> TYPE: PRT
<213> ORGANISM: Homo sapiens

<400> SEQUENCE: 1

Met Asn Gln Ser Ile Pro Val Ala Pro Thr Pro Pro Arg Arg Val Arg
1               5                   10                  15

Leu Lys Pro Trp Leu Val Ala Gln Val Asn Ser Cys Gln Tyr Pro Gly
            20                  25                  30

Leu Gln Trp Val Asn Gly Glu Lys Lys Leu Phe Cys Ile Pro Trp Arg
        35                  40                  45

His Ala Thr Arg His Gly Pro Ser Gln Asp Gly Asp Asn Thr Ile Phe
    50                  55                  60

Lys Ala Trp Ala Lys Glu Thr Gly Lys Tyr Thr Glu Gly Val Asp Glu
65                  70                  75                  80

Ala Asp Pro Ala Lys Trp Lys Ala Asn Leu Arg Cys Ala Leu Asn Lys
                85                  90                  95

Ser Arg Asp Phe Arg Leu Ile Tyr Asp Gly Pro Arg Asp Met Pro Pro
            100                 105                 110

Gln Pro Tyr Lys Ile Tyr Glu Val Cys Ser Asn Gly Pro Ala Pro Thr
        115                 120                 125
```

Asp Ser Gln Pro Pro Glu Asp Tyr Ser Phe Gly Ala Gly Glu Glu
    130                 135                 140

Glu Glu Glu Glu Glu Leu Gln Arg Met Leu Pro Ser Leu Ser Leu Thr
145                 150                 155                 160

Glu Asp Val Lys Trp Pro Pro Thr Leu Gln Pro Pro Thr Leu Arg Pro
                165                 170                 175

Pro Thr Leu Gln Pro Pro Thr Leu Gln Pro Val Val Leu Gly Pro
        180                 185                 190

Pro Ala Pro Asp Pro Ser Pro Leu Ala Pro Pro Gly Asn Pro Ala
    195                 200                 205

Gly Phe Arg Glu Leu Leu Ser Glu Val Leu Glu Pro Gly Pro Leu Pro
210                 215                 220

Ala Ser Leu Pro Pro Ala Gly Glu Gln Leu Leu Pro Asp Leu Leu Ile
225                 230                 235                 240

Ser Pro His Met Leu Pro Leu Thr Asp Leu Glu Ile Lys Phe Gln Tyr
                245                 250                 255

Arg Gly Arg Pro Pro Arg Ala Leu Thr Ile Ser Asn Pro His Gly Cys
                260                 265                 270

Arg Leu Phe Tyr Ser Gln Leu Glu Ala Thr Gln Glu Gln Val Glu Leu
                275                 280                 285

Phe Gly Pro Ile Ser Leu Glu Gln Val Arg Phe Pro Ser Pro Glu Asp
290                 295                 300

Ile Pro Ser Asp Lys Gln Arg Phe Tyr Thr Asn Gln Leu Leu Asp Val
305                 310                 315                 320

Leu Asp Arg Gly Leu Ile Leu Gln Leu Gln Gly Gln Asp Leu Tyr Ala
                325                 330                 335

Ile Arg Leu Cys Gln Cys Lys Val Phe Trp Ser Gly Pro Cys Ala Ser
                340                 345                 350

Ala His Asp Ser Cys Pro Asn Pro Ile Gln Arg Glu Val Lys Thr Lys
                355                 360                 365

Leu Phe Ser Leu Glu His Phe Leu Asn Glu Leu Ile Leu Phe Gln Lys
370                 375                 380

Gly Gln Thr Asn Thr Pro Pro Phe Glu Ile Phe Phe Cys Phe Gly
385                 390                 395                 400

Glu Glu Trp Pro Asp Arg Lys Pro Arg Glu Lys Lys Leu Ile Thr Val
                405                 410                 415

Gln Val Val Pro Val Ala Ala Arg Leu Leu Glu Met Phe Ser Gly
                420                 425                 430

Glu Leu Ser Trp Ser Ala Asp Ser Ile Arg Leu Gln Ile Ser Asn Pro
    435                 440                 445

Asp Leu Lys Asp Arg Met Val Glu Gln Phe Lys Glu Leu His His Ile
450                 455                 460

Trp Gln Ser Gln Gln Arg Leu Gln Pro Val Ala Gln Ala Pro Pro Gly
465                 470                 475                 480

Ala Gly Leu Gly Val Gly Gln Gly Pro Trp Pro Met His Pro Ala Gly
                485                 490                 495

Met Gln

<210> SEQ ID NO 2
<211> LENGTH: 504
<212> TYPE: PRT
<213> ORGANISM: Homo sapiens

<400> SEQUENCE: 2

```
Met Asn Gln Ser Ile Pro Val Ala Pro Thr Pro Arg Arg Val Arg
1               5                   10                  15

Leu Lys Pro Trp Leu Val Ala Gln Val Asn Ser Cys Gln Tyr Pro Gly
                20                  25                  30

Leu Gln Trp Val Asn Gly Glu Lys Lys Leu Phe Cys Ile Pro Trp Arg
            35                  40                  45

His Ala Thr Arg His Gly Pro Ser Gln Asp Gly Asp Asn Thr Ile Phe
50                      55                  60

Lys Ala Trp Ala Lys Glu Thr Gly Lys Tyr Thr Glu Gly Val Asp Glu
65                  70                  75                  80

Ala Asp Pro Ala Lys Trp Lys Ala Asn Leu Arg Cys Ala Leu Asn Lys
                85                  90                  95

Ser Arg Asp Phe Arg Leu Ile Tyr Asp Gly Pro Arg Asp Met Pro Pro
                100                 105                 110

Gln Pro Tyr Lys Ile Tyr Glu Val Cys Ser Asn Gly Pro Ala Pro Thr
            115                 120                 125

Asp Ser Gln Pro Pro Glu Asp Tyr Ser Phe Gly Ala Gly Glu Glu Glu
        130                 135                 140

Glu Glu Glu Glu Glu Leu Gln Arg Met Leu Pro Ser Leu Ser Leu Thr
145                 150                 155                 160

Asp Ala Val Gln Ser Gly Pro His Met Thr Pro Tyr Ser Leu Leu Lys
                165                 170                 175

Glu Asp Val Lys Trp Pro Pro Thr Leu Gln Pro Pro Thr Leu Gln Pro
            180                 185                 190

Pro Val Val Leu Gly Pro Pro Ala Pro Asp Pro Ser Pro Leu Ala Pro
        195                 200                 205

Pro Pro Gly Asn Pro Ala Gly Phe Arg Glu Leu Leu Ser Glu Val Leu
210                 215                 220

Glu Pro Gly Pro Leu Pro Ala Ser Leu Pro Pro Ala Gly Glu Gln Leu
225             230                 235                 240

Leu Pro Asp Leu Leu Ile Ser Pro His Met Leu Pro Leu Thr Asp Leu
                245                 250                 255

Glu Ile Lys Phe Gln Tyr Arg Gly Arg Pro Pro Arg Ala Leu Thr Ile
            260                 265                 270

Ser Asn Pro His Gly Cys Arg Leu Phe Tyr Ser Gln Leu Glu Ala Thr
    275                 280                 285

Gln Glu Gln Val Glu Leu Phe Gly Pro Ile Ser Leu Glu Gln Val Arg
    290                 295                 300

Phe Pro Ser Pro Glu Asp Ile Pro Ser Asp Lys Gln Arg Phe Tyr Thr
305                 310                 315                 320

Asn Gln Leu Leu Asp Val Leu Asp Arg Gly Leu Ile Leu Gln Leu Gln
                325                 330                 335

Gly Gln Asp Leu Tyr Ala Ile Arg Leu Cys Gln Cys Lys Val Phe Trp
            340                 345                 350

Ser Gly Pro Cys Ala Ser Ala His Asp Ser Cys Pro Asn Pro Ile Gln
        355                 360                 365

Arg Glu Val Lys Thr Lys Leu Phe Ser Leu Glu His Phe Leu Asn Glu
    370                 375                 380

Leu Ile Leu Phe Gln Lys Gly Gln Thr Asn Thr Pro Pro Phe Glu
385                 390                 395                 400

Ile Phe Phe Cys Phe Gly Glu Glu Trp Pro Asp Arg Lys Pro Arg Glu
                405                 410                 415
```

```
Lys Lys Leu Ile Thr Val Gln Val Val Pro Val Ala Ala Arg Leu Leu
            420                 425                 430

Leu Glu Met Phe Ser Gly Glu Leu Ser Trp Ser Ala Asp Ser Ile Arg
        435                 440                 445

Leu Gln Ile Ser Asn Pro Asp Leu Lys Asp Arg Met Val Glu Gln Phe
    450                 455                 460

Lys Glu Leu His His Ile Trp Gln Ser Gln Gln Arg Leu Gln Pro Val
465                 470                 475                 480

Ala Gln Ala Pro Pro Gly Ala Gly Leu Gly Val Gly Gln Gly Pro Trp
                485                 490                 495

Pro Met His Pro Ala Gly Met Gln
            500

<210> SEQ ID NO 3
<211> LENGTH: 2778
<212> TYPE: DNA
<213> ORGANISM: Homo sapiens

<400> SEQUENCE: 3
gtccagctgc gcctggaaag cgagctcgga cccctctgcc atgaaccagt ccatcccagt      60
ggctcccacc ccaccccgcc gcgtgcggct gaagccctgg ctggtggccc aggtgaacag     120
ctgccagtac ccagggcttc aatgggtcaa cggggaaaag aaattattct gcatcccctg     180
gaggcatgcc acaaggcatg gtcccagcca ggacggagat aacaccatct tcaaggcctg     240
ggccaaggag acagggaaat acaccgaagg cgtggatgaa gccgatccgg ccaagtggaa     300
ggccaacctg cgctgtgccc ttaacaagag ccgggacttc cgcctcatct acgacgggcc     360
ccgggacatg ccacctcagc cctacaagat ctacgaggtc tgctccaatg ccctgctcc     420
cacagactcc cagccccctg aggattactc ttttggtgca ggagaggagg aggaagaaga     480
ggaagagctg cagaggatgt tgccaagcct gagcctcaca gaggatgtca gtggccgcc     540
cactctgcag ccgcccactc tgcggccgcc tactctgcag ccgcccactc tgcagccgcc     600
cgtggtgctg ggtccccctg ctccagaccc cagcccctg gctcctcccc ctggcaaccc     660
tgctggcttc agggagcttc tctctgaggt cctggagcct gggcccctgc ctgccagcct     720
gcccctgca ggcgaacagc tcctgccaga cctgctgatc agccccaca tgctgcctct     780
gaccgacctg gagatcaagt ttcagtaccg gggcggcca cccgggccc tcaccatcag     840
caaccccat ggctgccggc tcttctacag ccagctggag gccacccagg agcaggtgga     900
actcttcggc cccataagcc tggagcaagt gcgcttcccc agccctgagg acatccccag     960
tgacaagcag cgcttctaca cgaaccagct gctggatgtc ctggaccgcg ggctcatcct    1020
ccagctacag ggccaggacc tttatgccat ccgcctgtgt cagtgcaagg tgttctggag    1080
cgggccttgt gcctcagccc atgactcatg ccccaacccc atccagcggg aggtcaagac    1140
caagcttttc agcctggagc attttctcaa tgagctcatc ctgttccaaa agggccagac    1200
caacaccccc accccttcg agatcttctt ctgctttggg gaagaatggc ctgaccgcaa    1260
accccgagag aagaagctca ttactgtaca ggtggtgcct gtagcagctc gactgctgct    1320
ggagatgttc tcaggggagc tatcttggtc agctgatagt atccggctac agatctcaaa    1380
cccagacctc aaagaccgca tggtggagca attcaaggag ctccatcaca tctggcagtc    1440
ccagcagcgg ttgcagcctg tgcccaggcc ccctcctgga gcaggccttg gtgttggcca    1500
ggggccctgg cctatgcacc cagctggcat gcaataacaa ggctgcagac ggtgactggc    1560
cctggcttcc tgggtggcgg tgcggactga gtgtggagatg tgacagcccc gatgagcacc    1620
```

-continued

| | |
|---|---|
| tggctggctg cagggtccta cctctgggtt tcctggaagt ggatttgggc caagaaggag | 1680 |
| agggagaaag gcccgagccc ctgccttccc gggcctttct ctcctgggct gtctctggtc | 1740 |
| tggtcagcct ggctctcggg aaattcagcc atgagcaggg aaagaactct cccaaccctg | 1800 |
| gggcctagct gtataggagg aattgcctaa gggtggccca ctcttgtgat tgccccattt | 1860 |
| cctctggcaa caaaagccag agtgttgtgg gccaagtccc cccacagggc ctctgcaggg | 1920 |
| catggccctg atttccctgg tttgagactc acttcctcat ctccctgtcc tctgagataa | 1980 |
| tatgagtgag cacttaggta tcatatcaga tgctcaaggc tggcagctac ccccttcttg | 2040 |
| agagtccaag aacctggagc agaaataatt tttatgtatt tttggattaa tgaatgttaa | 2100 |
| aaacagactc agctgtttct ttccttttac tactaccagt tgctcccatg ctgctccacc | 2160 |
| aggccctgtt tcggatgcca actggcccac tccccaagca cttgccccca gcttgcgacc | 2220 |
| attggcactg ggagggcctg gcttctgggc tgatgggtca gttgggcctt cataaacact | 2280 |
| cacctgctg gctttgcctt ccaggaggaa gctggctgaa gcaagggtgt ggaattttaa | 2340 |
| atgtgtgcac agtctggaaa actgtcagaa tcagttttcc cataaagggg tgggctagca | 2400 |
| ttgcagctgc atttgggacc attcaaatct gtcactctct tgtgtatatt cctgtgctat | 2460 |
| taaatatatc agggcagtgc atgtaaatca tcctgatata tttaatatat ttattatatt | 2520 |
| gtcccccgag gtggggacag tgagtgagtt ctcttagtcc ccccagagct ggttgttaaa | 2580 |
| gagcctggca cctacccgct ctcacttcat ctgtgtcatc tctgcacact ccagcccact | 2640 |
| ttctgccttc agccattgag tggaagctgc cccaggccct taccaggtgc agatgcccaa | 2700 |
| tcttgatgcc cagccatcag aactgtgagc caaataaacc ttttttctgta taaattaccc | 2760 |
| aaaaaaaaaa aaaaaaaa | 2778 |

<210> SEQ ID NO 4
<211> LENGTH: 2786
<212> TYPE: DNA
<213> ORGANISM: Homo sapiens

<400> SEQUENCE: 4

| | |
|---|---|
| gcttggtccc gccgcccggc cggtgctccc tggcgcagcc acgcaggcgc accgcagaca | 60 |
| gaccccctctg ccatgaacca gtccatccca gtggctccca ccccaccccg ccgcgtgcgg | 120 |
| ctgaagccct ggctggtggc ccaggtgaac agctgccagt acccagggct tcaatgggtc | 180 |
| aacggggaaa agaaattatt ctgcatcccc tggaggcatg ccacaaggca tggtcccagc | 240 |
| caggacggag ataacaccat cttcaaggcc tgggccaagg agacagggaa atacaccgaa | 300 |
| ggcgtggatg aagccgatcc ggccaagtgg aaggccaacc tgcgctgtgc ccttaacaag | 360 |
| agccgggact tccgcctcat ctacgacggg cccggagaca tgccacctca gcctacaag | 420 |
| atctacgagg tctgctccaa tggccctgct cccacagact cccagccccc tgaggattac | 480 |
| tcttttggtg caggagagga ggaggaagaa gaggaagagc tgcagaggat gttgccaagc | 540 |
| ctgagcctca cagaggatgt caagtggccg cccactctgc agccgcccac tctgcggccg | 600 |
| cctactctgc agccgcccac tctgcagccg ccgtggtgc tgggtccccc tgctccagac | 660 |
| cccagccccc tggctcctcc ccctggcaac cctgctggct tcaggagct tctctctgag | 720 |
| gtcctggagc ctgggcccct gcctgccagc ctgcccctg caggcgaaca gctcctgcca | 780 |
| gacctgctga tcagccccca catgctgcct ctgaccgacc tggagatcaa gttcagtac | 840 |
| cgggggcggc cacccgggc cctcaccatc agcaacccc atggctgccg gctcttctac | 900 |

|                                                                                      |      |
|--------------------------------------------------------------------------------------|------|
| agccagctgg aggccaccca ggagcaggtg gaactcttcg gccccataag cctggagcaa                    | 960  |
| gtgcgcttcc ccagccctga ggacatcccc agtgacaagc agcgcttcta cacgaaccag                    | 1020 |
| ctgctggatg tcctggaccg cgggctcatc ctccagctac agggccagga cctttatgcc                    | 1080 |
| atccgcctgt gtcagtgcaa ggtgttctgg agcgggcctt gtgcctcagc ccatgactca                    | 1140 |
| tgccccaacc ccatccagcg ggaggtcaag accaagcttt tcagcctgga gcattttctc                    | 1200 |
| aatgagctca tcctgttcca aaagggccag accaacaccc caccacccctt cgagatcttc                   | 1260 |
| ttctgctttg gggaagaatg gcctgaccgc aaaccccgag agaagaagct cattactgta                    | 1320 |
| caggtggtgc ctgtagcagc tcgactgctg ctggagatgt tctcagggga gctatcttgg                    | 1380 |
| tcagctgata gtatccggct acagatctca aacccagacc tcaaagaccg catggtggag                    | 1440 |
| caattcaagg agctccatca catctggcag tcccagcagc ggttgcagcc tgtggcccag                    | 1500 |
| gcccctcctg gagcaggcct tggtgttggc caggggccct ggcctatgca cccagctggc                    | 1560 |
| atgcaataac aaggctgcag acggtgactg gccctggctt cctgggtggc ggtgcggact                    | 1620 |
| gatgtggaga tgtgacagcc ccgatgagca cctggctggc tgcaggggtcc tacctctggg                   | 1680 |
| tttcctggaa gtggatttgg gccaagaagg agagggagaa aggcccgagc ccctgccttc                    | 1740 |
| ccgggccttt ctctcctggg ctgtctctgg tctggtcagc ctggctctcg ggaaattcag                    | 1800 |
| ccatgagcag ggaaagaact ctcccaaccc tggggcctag ctgtatagga ggaattgcct                    | 1860 |
| aagggtggcc cactcttgtg attgccccat ttcctctggc aacaaaagcc agagtgttgt                    | 1920 |
| gggccaagtc cccccacagg gcctctgcag ggcatggccc tgatttccct ggtttgagac                    | 1980 |
| tcacttcctc atctccctgt cctctgagat aatatgagtg agcacttagg tatcatatca                    | 2040 |
| gatgctcaag gctggcagct accccctttct tgagagtcca agaacctgga gcagaaataa                   | 2100 |
| tttttatgta ttttttggatt aatgaatgtt aaaaacagac tcagctgttt ctttcctttt                   | 2160 |
| actactacca gttgctccca tgctgctcca ccaggccctg tttcggatgc caactggccc                    | 2220 |
| actcccaag cacttgcccc cagcttgcga ccattggcac tgggagggcc tggcttctgg                     | 2280 |
| gctgatgggt cagttgggcc ttcataaaca ctcacctggc tggctttgcc ttccaggagg                    | 2340 |
| aagctggctg aagcaagggt gtggaatttt aaatgtgtgc acagtctgga aaactgtcag                    | 2400 |
| aatcagtttt cccataaaag ggtgggctag cattgcagct gcatttggga ccattcaaat                    | 2460 |
| ctgtcactct cttgtgtata ttcctgtgct attaaatata tcagggcagt gcatgtaaat                    | 2520 |
| catcctgata tatttaatat atttattata ttgtcccccg aggtggggac agtgagtgag                    | 2580 |
| ttctcttagt ccccccagag ctggttgtta aagagcctgg cacctacccg ctctcacttc                    | 2640 |
| atctgtgtca tctctgcaca ctccagccca cttctctgcct tcagccattg agtggaagct                   | 2700 |
| gccccaggcc cttaccaggt gcagatgccc aatcttgatg cccagccatc agaactgtga                    | 2760 |
| gccaaataaa ccttttttctg tataaa                                                        | 2786 |

<210> SEQ ID NO 5
<211> LENGTH: 1497
<212> TYPE: DNA
<213> ORGANISM: Homo sapiens

<400> SEQUENCE: 5

|                                                                                      |      |
|--------------------------------------------------------------------------------------|------|
| atgaaccagt ccatcccagt ggctcccacc ccaccccgcc gcgtgcggct gaagccctgg                    | 60   |
| ctggtggccc aggtgaacag ctgccagtac ccagggcttc aatgggtcaa cggggaaaag                    | 120  |
| aaattattct gcatccctg gaggcatgcc acaaggcatg gtcccagcca ggacggagat                     | 180  |
| aacaccatct tcaaggcctg ggccaaggag acagggaaat acaccgaagg cgtggatgaa                    | 240  |

```
gccgatccgg ccaagtggaa ggccaacctg cgctgtgccc ttaacaagag ccgggacttc    300
cgcctcatct acgacgggcc ccgggacatg ccacctcagc cctacaagat ctacgaggtc    360
tgctccaatg ccctgctcc cacagactcc cagcccctg aggattactc ttttggtgca     420 ggagaggag aggaagaaga ggaagagctg cagaggatgt tgccaagcct gagcctcaca     480
gaggatgtca agtggccgcc cactctgcag ccgcccactc tgcggccgcc tactctgcag    540
ccgcccactc tgcagccgcc cgtggtgctg gtccccctg ctccagaccc cagcccctg     600 gctcctcccc ctggcaaccc tgctggcttc agggagcttc tctctgaggt cctggagcct    660
gggcccctgc ctgccagcct gcccctgca ggcgaacagc tcctgccaga cctgctgatc     720
agcccccaca tgctgcctct gaccgacctg gagatcaagt ttcagtaccg ggggcggcca    780
ccccggggcc tcaccatcag caaccccat ggctgccggc tcttctacag ccagctggag    840
gccacccagg agcaggtgga actcttcggc cccataagcc tggagcaagt gcgcttcccc    900
agccctgagg acatccccag tgacaagcag cgcttctaca cgaaccagct gctggatgtc    960
ctggaccgcg ggctcatcct ccagctacag ggccaggacc tttatgccat ccgcctgtgt   1020
cagtgcaagg tgttctggag cgggccttgt gcctcagccc atgactcatg ccccaacccc   1080
atccagcggg aggtcaagac caagcttttc agcctggagc attttctcaa tgagctcatc   1140
ctgttccaaa agggccagac caacacccca ccaccttcg agatcttctt ctgctttggg   1200
gaagaatggc ctgaccgcaa accccgagag aagaagctca ttactgtaca ggtggtgcct   1260
gtagcagctc gactgctgct ggagatgttc tcaggggagc tatcttggtc agctgatagt   1320
atccggctac agatctcaaa cccagacctc aaagaccgca tggtggagca attcaaggag   1380
ctccatcaca tctggcagtc ccagcagcgg ttgcagcctg tggcccaggc ccctcctgga   1440
gcaggccttg tgttggcca ggggccctgg cctatgcacc cagctggcat gcaataa      1497
```

<210> SEQ ID NO 6
<211> LENGTH: 498
<212> TYPE: PRT
<213> ORGANISM: Homo sapiens

<400> SEQUENCE: 6

```
Met Asn Gln Ser Ile Pro Val Ala Pro Thr Pro Pro Arg Arg Val Arg
1               5                   10                  15

Leu Lys Pro Trp Leu Val Ala Gln Val Asn Ser Cys Gln Tyr Pro Gly
                20                  25                  30

Leu Gln Trp Val Asn Gly Glu Lys Lys Leu Phe Cys Ile Pro Trp Arg
            35                  40                  45

His Ala Thr Arg His Gly Pro Ser Gln Asp Gly Asp Asn Thr Ile Phe
        50                  55                  60

Lys Ala Trp Ala Lys Glu Thr Gly Lys Tyr Thr Glu Gly Val Asp Glu
65                  70                  75                  80

Ala Asp Pro Ala Lys Trp Lys Ala Asn Leu Arg Cys Ala Leu Asn Lys
                85                  90                  95

Ser Arg Asp Phe Arg Leu Ile Tyr Asp Gly Pro Arg Asp Met Pro Pro
                100                 105                 110

Gln Pro Tyr Lys Ile Tyr Glu Val Cys Ser Asn Gly Pro Ala Pro Thr
            115                 120                 125

Asp Ser Gln Pro Pro Glu Asp Tyr Ser Phe Gly Ala Gly Glu Glu Glu
        130                 135                 140

Glu Glu Glu Glu Glu Leu Gln Arg Met Leu Pro Ser Leu Ser Leu Thr
```

```
            145                 150                 155                 160
        Glu Asp Val Lys Trp Pro Pro Thr Leu Gln Pro Pro Thr Leu Arg Pro
                        165                 170                 175
        Pro Thr Leu Gln Pro Pro Thr Leu Gln Pro Val Val Leu Gly Pro
                        180                 185                 190
        Pro Ala Pro Asp Pro Ser Pro Leu Ala Pro Pro Gly Asn Pro Ala
                        195                 200                 205
        Gly Phe Arg Glu Leu Leu Ser Glu Val Leu Glu Pro Gly Pro Leu Pro
        210                     215                 220
        Ala Ser Leu Pro Pro Ala Gly Glu Gln Leu Leu Pro Asp Leu Leu Ile
        225                     230                 235                 240
        Ser Pro His Met Leu Pro Leu Thr Asp Leu Glu Ile Lys Phe Gln Tyr
                        245                 250                 255
        Arg Gly Arg Pro Pro Arg Ala Leu Thr Ile Ser Asn Pro His Gly Cys
                        260                 265                 270
        Arg Leu Phe Tyr Ser Gln Leu Glu Ala Thr Gln Glu Gln Val Glu Leu
                        275                 280                 285
        Phe Gly Pro Ile Ser Leu Glu Gln Val Arg Phe Pro Ser Pro Glu Asp
        290                     295                 300
        Ile Pro Ser Asp Lys Gln Arg Phe Tyr Thr Asn Gln Leu Leu Asp Val
        305                     310                 315                 320
        Leu Asp Arg Gly Leu Ile Leu Gln Leu Gln Gly Gln Asp Leu Tyr Ala
                        325                 330                 335
        Ile Arg Leu Cys Gln Cys Lys Val Phe Trp Ser Gly Pro Cys Ala Ser
                        340                 345                 350
        Ala His Asp Ser Cys Pro Asn Pro Ile Gln Arg Glu Val Lys Thr Lys
                        355                 360                 365
        Leu Phe Ser Leu Glu His Phe Leu Asn Glu Leu Ile Leu Phe Gln Lys
                        370                 375                 380
        Gly Gln Thr Asn Thr Pro Pro Phe Glu Ile Phe Phe Cys Phe Gly
        385                     390                 395                 400
        Glu Glu Trp Pro Asp Arg Lys Pro Arg Glu Lys Lys Leu Ile Thr Val
                        405                 410                 415
        Gln Val Val Pro Val Ala Ala Arg Leu Leu Glu Met Phe Ser Gly
                        420                 425                 430
        Glu Leu Ser Trp Ser Ala Asp Ser Ile Arg Leu Gln Ile Ser Asn Pro
                        435                 440                 445
        Asp Leu Lys Asp Arg Met Val Glu Gln Phe Lys Glu Leu His His Ile
        450                     455                 460
        Trp Gln Ser Gln Gln Arg Leu Gln Pro Val Ala Gln Ala Pro Pro Gly
        465                     470                 475                 480
        Ala Gly Leu Gly Val Gly Gln Gly Pro Trp Pro Met His Pro Ala Gly
                        485                 490                 495
        Met Gln

<210> SEQ ID NO 7
<211> LENGTH: 25
<212> TYPE: RNA
<213> ORGANISM: Homo sapiens
<220> FEATURE:
<221> NAME/KEY: misc_feature
<222> LOCATION: (24)..(25)
<223> OTHER INFORMATION: n is a, c, g, or u

<400> SEQUENCE: 7
```

```
gaagaagcuc auuacuguac aggnn                                          25

<210> SEQ ID NO 8
<211> LENGTH: 27
<212> TYPE: RNA
<213> ORGANISM: Homo sapiens

<400> SEQUENCE: 8
caccuguaca guaaugagcu ucuucuc                                        27

<210> SEQ ID NO 9
<211> LENGTH: 8
<212> TYPE: PRT
<213> ORGANISM: Artificial Sequence
<220> FEATURE:
<223> OTHER INFORMATION: IRF5-binding Cell Penetrating Peptide
<220> FEATURE:
<221> NAME/KEY: MISC_FEATURE
<222> LOCATION: (2)..(2)
<223> OTHER INFORMATION: W or A
<220> FEATURE:
<221> NAME/KEY: MISC_FEATURE
<222> LOCATION: (3)..(3)
<223> OTHER INFORMATION: L or T
<220> FEATURE:
<221> NAME/KEY: MISC_FEATURE
<222> LOCATION: (4)..(4)
<223> OTHER INFORMATION: L, A, D, or F
<220> FEATURE:
<221> NAME/KEY: MISC_FEATURE
<222> LOCATION: (6)..(6)
<223> OTHER INFORMATION: L, G, or T
<220> FEATURE:
<221> NAME/KEY: MISC_FEATURE
<222> LOCATION: (7)..(7)
<223> OTHER INFORMATION: F, L, or M

<400> SEQUENCE: 9

Tyr Xaa Xaa Xaa Leu Xaa Xaa Val
1               5

<210> SEQ ID NO 10
<211> LENGTH: 10
<212> TYPE: PRT
<213> ORGANISM: Artificial Sequence
<220> FEATURE:
<223> OTHER INFORMATION: IRF5-binding Cell Penetrating Peptide
<220> FEATURE:
<221> NAME/KEY: MISC_FEATURE
<222> LOCATION: (3)..(3)
<223> OTHER INFORMATION: L or D
<220> FEATURE:
<221> NAME/KEY: MISC_FEATURE
<222> LOCATION: (6)..(7)
<223> OTHER INFORMATION: amino acids 6 and 7 are, in order, Q-W or R-F
<220> FEATURE:
<221> NAME/KEY: MISC_FEATURE
<222> LOCATION: (6)..(7)
<223> OTHER INFORMATION: residues 6 and 7 are, in order, Q-W or R-F

<400> SEQUENCE: 10

Lys Asp Xaa Met Val Xaa Xaa Phe Lys Asp
1               5                   10
```